(12) United States Patent
Luo et al.

(10) Patent No.: US 12,077,513 B2
(45) Date of Patent: Sep. 3, 2024

(54) PROCESS ROUTE OF COMPOUND OF FORMULA (IV), CRYSTAL FORM AND PREPARATION METHOD THEREFOR

(71) Applicant: SHANDONG DANHONG PHARMACEUTICAL CO., LTD., Shandong (CN)

(72) Inventors: Zhi Luo, Shanghai (CN); Xiaolin Li, Shanghai (CN); Yaxun Yang, Shanghai (CN); Lele Yang, Shanghai (CN); Peng Li, Shanghai (CN); Haiying He, Shanghai (CN); Jian Li, Shanghai (CN); Shuhui Chen, Shanghai (CN)

(73) Assignee: SHANDONG DANHONG PHARMACEUTICAL CO., LTD., Shandong (CN)

( * ) Notice: Subject to any disclaimer, the term of this patent is extended or adjusted under 35 U.S.C. 154(b) by 729 days.

(21) Appl. No.: 17/311,431

(22) PCT Filed: Dec. 20, 2019

(86) PCT No.: PCT/CN2019/127155
§ 371 (c)(1),
(2) Date: Jun. 7, 2021

(87) PCT Pub. No.: WO2020/125776
PCT Pub. Date: Jun. 25, 2020

(65) Prior Publication Data
US 2022/0024880 A1   Jan. 27, 2022

(30) Foreign Application Priority Data
Dec. 20, 2018   (CN) .......................... 201811565301.3

(51) Int. Cl.
*C07D 249/08*   (2006.01)

(52) U.S. Cl.
CPC ........ *C07D 249/08* (2013.01); *C07B 2200/13* (2013.01)

(58) Field of Classification Search
CPC .......................... C07D 249/08; C07B 2200/13
See application file for complete search history.

(56) References Cited

U.S. PATENT DOCUMENTS

| 2007/0293548 A1 | 12/2007 | Wang et al. |
| 2020/0087248 A1 | 3/2020 | Zhu et al. |
| 2020/0115352 A1 | 4/2020 | Luo et al. |

FOREIGN PATENT DOCUMENTS

| WO | 2007120528 A2 | 10/2007 |
| WO | 2013163675 A1 | 11/2013 |

(Continued)

OTHER PUBLICATIONS

Tacon et al., "Synthesis, biological evaluation and mechanistic studies of totarol amino alcohol derivatives as potential antimalarial agents", Bioorganic & Medicinal Chemistry, vol. 20, (2021, pp. 893-902.

(Continued)

*Primary Examiner* — Matthew P Coughlin
*Assistant Examiner* — Ashli Ariana Chicks
(74) *Attorney, Agent, or Firm* — MH2 TECHNOLOGY LAW GROUP LLP

(57) ABSTRACT

Disclosed are a process route of a compound of a compound of formula (IV), a crystal form and a preparation method therefor. Also disclosed is an application of the crystal form in preparation of drugs for treating diseases associated with SSAO.

(Continued)

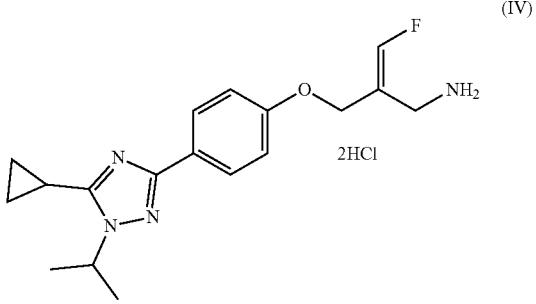

(IV) 2HCl

16 Claims, 8 Drawing Sheets

(56) References Cited

FOREIGN PATENT DOCUMENTS

| WO | 2018158140 | A1 | | 9/2018 | |
|---|---|---|---|---|---|
| WO | 2018196677 | A1 | | 11/2018 | |
| WO | WO-2018233633 | A1 | * | 12/2018 | ......... A61K 31/4196 |
| WO | 2019024924 | A1 | | 2/2019 | |
| WO | 2019241751 | A1 | | 12/2019 | |

OTHER PUBLICATIONS

Perez et al., "Regioselective Synthesis of 1,2,4-Triazole and 1,2,4-Oxadiazole Derivatives", Synthesis, vol. 6 (Jun. 1983), pp. 483-486.

Chinese First Office Action issued Mar. 31, 2022 in corresponding Chinese Application No. 201980066989.7, 9 pages (includes English translation).
Lunniss, Christopher, First Office Action dated Nov. 15, 2022, Australian application No. 2019408509, 4 pages.
Notice of Preliminary Rejection issued in Korean Patent Application No. 10-2021-7022942 dated Apr. 3, 2023, with English language translation, 11 pages.
European Office Action issued in European Patent Application No. 19897902.3 dated Jul. 19, 2023, 4 pages.
2nd Office Action (with English Translation) issued in Chinese Patent Application No. 2019800669897 mailed on Sep. 22, 2022, 18 pages.
EESR issued in European Patent Application No. 19897902.3 mailed on Aug. 18, 2022, 8 pages.
1st Office Action (with English Translation) issued in Japanese Patent Application No. 2021-536243 mailed on Aug. 2, 2022, 13 pages.
Noriaki Hirayama, Handbook of Organic Compound Crystal Preparation—Principles and Tips—, Maruzen Co., Ltd., Jul. 25, 2008, pp. 57-84.
Giuseppe Romeo et al., "New Pyrimido[5,4-b]indoles as Ligands for α1-Adrenoceptor Subtypes", J. Med.Chem., 2003, vol. 46, No. 14, p. 2877-2894.
International Search Report (with English Translation) issued in International Patent Application No. PCT/CN2019/127155 mailed on Mar. 27, 2020, 8 pages.
Written Opinion (with English Translation) of the International Searching Authority issued in International Patent Application No. PCT/CN2019/127155 mailed on Mar. 27, 2020, 13 pages.
English Translation of Priority Document of Chinese Application No. 201811565301.3 filed on Dec. 20, 2018, 27 pages.
Decision of Final Rejection dated Jan. 9, 2023, Chinese Patent Application No. 201980066989.7, 12 pages (including English translation).

* cited by examiner

PROCESS ROUTE OF COMPOUND OF FORMULA (IV), CRYSTAL FORM AND PREPARATION METHOD THEREFOR

CROSS-REFERENCE TO RELATED APPLICATION(S)

This application is a national stage entry from International Application No. PCT/CN2019/127155, filed on Dec. 20, 2019, in the Receiving Office ("RO/CN") of the China National Intellectual Property Administration ("CNIPA"), published as International Publication No. WO 2020/125776 A1 on Jun. 25, 2020. International Application No. PCT/CN2019/127155 claims priority under 35 U.S.C. § 119 from Chinese Patent Application No. 201811565301.3, filed on Dec. 20, 2018, in the CNIPA, the entire contents of all of which are incorporated herein by reference.

The present disclosure claims the following right of priority:

CN201811565301.3, filing date: 20 Dec. 2018.

TECHNICAL FIELD

The present disclosure relates to a process route of compound of formula (IV), crystal form and preparation method therefor, as well as to a use of the crystal form in the preparation of drugs for treating diseases associated with SSAO.

BACKGROUND

In most organisms, including humans, two groups of mammalian amine oxidases metabolize various endogenously produced or exogenously absorbed monoamine-, diamine- and polyamines. These include monoamine oxidases (MAO-A and MAO-B) that are present in the mitochondria of most cell types and use covalently bonded flavin adenine dinucleotide (FAD) as a cofactor. Polyamine oxidase is another FAD-dependent amine oxidase that oxidizes deaminated spermine and spermidine. SSAO/VAP-1 belongs to the second group of copper-dependent and uses other cofactors such as oxidized tyrosine residues (abbreviated as TPQ or LTQ) in addition to FAD. The oxidative deamination of MAO and SSAO/VAP-1 includes some common substrates of monoamines such as dopamine, tyramine, and benzylamine. SSAO/VAP-1 also oxidizes endogenous methylamine and aminoacetone.

Semicarbazide-sensitive amine oxidase (SSAO), also known as primary amine oxidase, plasma amine oxidase, and benzylamine oxidase, is structurally the same as vascular adhesion protein-1 (VAP-1). SSAO/VAP-1 is used to describe the protein.

These enzymes were originally defined by the ability of some compounds to inhibit their enzymatic activity. For example, MAO-A is selectively inhibited by chlorgiline, and MAO-B is selectively inhibited by L-deprenyl, although neither chlorgiline nor L-deprenyl can inhibit the amine oxidase activity of SSAO/VAP-1. SSAO/VAP-1 can be inhibited by semicarbazide, hence named as semicarbazide sensitive amine oxidase.

SSAO/VAP-1 is an extracellular enzyme that contains a very short cytoplasmic tail, a single transmembrane domain, and a large, highly glycosylated extracellular domain containing an active center for amine oxidase activity. SSAO/VAP-1 also exists in dissolved form circulating in the plasma of some animals. This form has been shown to be a fragmentation product of membrane-bonded SSAO/VAP-1.

SSAO/VAP-1 seems to have two physiological functions: the first is the above-mentioned amine oxidase activity and the second is the cell adhesion activity. Both activities are related to the inflammatory process. SSAO/VAP-1 has been shown to play an important role in the circulating extravasation of inflammatory cells from the site of inflammation. The VAP-1 antibody was confirmed to reduce the inflammatory process by blocking the adhesion site of SSAO/VAP-1 protein, and provided a lot of evidence of knockout in vitro and in vivo. It is now clear that SSAO/VAP-1 is an important inflammatory cell mediator.

WO2013163675 reported the compound PXS-4728A, the structure is as follows.

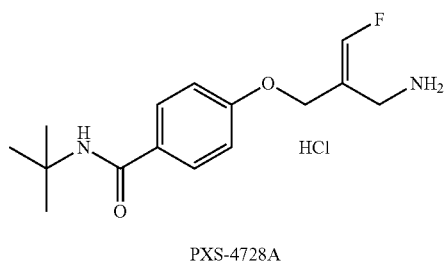 [SMILES: CC(C)(C)NC(=O)c1ccc(OC/C(=C/F)CN)cc1 ; Cl ; "PXS-4728A"]

PXS-4728A

Contents of the Present Invention

The present disclosure provides a crystal form A of a compound of formula (IV), the X-ray powder diffraction pattern of which has characteristic diffraction peaks at the following 2θ angles: 9.05±0.2°, 12.34±0.2°, 22.52±0.2°;

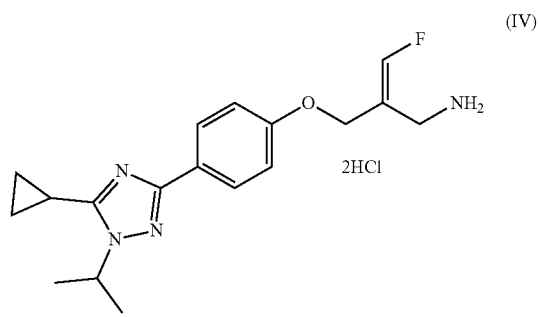 [SMILES: CC(C)n1nc(-c2ccc(OC/C(=C/F)CN)cc2)nc1C1CC1 ; "2HCl"]

In some embodiments of the present invention, the crystal form A of the compound of formula (IV) has characteristic diffraction peaks in its X-ray powder diffraction pattern at the following 2θ angles: 9.05±0.2°, 12.34±0.2°, 16.60±0.2°, 17.17±0.2°, 17.83±0.2°, 20.82±0.2°, 22.52±0.2°, 26.03±0.2°.

In some embodiments of the present invention, the XRPD pattern of the crystal form A of the compound of formula (IV) is shown in FIG. 1.

In some embodiments of the present invention, the XRPD pattern analysis data of the crystal form A of the compound of formula (IV) is shown in Table 1.

TABLE 1

XRPD pattern analysis data of crystal form A

| Number | 2θ angle (°) | Interplanar spacing (Å) | Relative strength (%) |
|---|---|---|---|
| 1 | 9.049 | 9.7641 | 100.0 |
| 2 | 11.908 | 7.4258 | 7.2 |
| 3 | 12.344 | 7.1644 | 63.9 |
| 4 | 13.313 | 6.6452 | 9.4 |
| 5 | 15.815 | 5.5990 | 9.1 |
| 6 | 16.604 | 5.3347 | 21.2 |
| 7 | 17.169 | 5.1602 | 7.8 |
| 8 | 17.827 | 4.9714 | 18.6 |
| 9 | 19.544 | 4.5384 | 6.9 |
| 10 | 20.823 | 4.2624 | 12.5 |
| 11 | 21.619 | 4.1073 | 2.8 |
| 12 | 22.522 | 3.9446 | 30.1 |
| 13 | 23.270 | 3.8194 | 14.0 |
| 14 | 23.861 | 3.7262 | 8.0 |
| 15 | 26.033 | 3.4199 | 42.4 |
| 16 | 27.214 | 3.2741 | 12.3 |
| 17 | 27.512 | 3.2393 | 16.7 |
| 18 | 28.220 | 3.1597 | 16.6 |
| 19 | 29.462 | 3.0292 | 15.2 |
| 20 | 29.878 | 2.9880 | 12.1 |
| 21 | 31.329 | 2.8529 | 4.1 |
| 22 | 33.233 | 2.6937 | 8.5 |
| 23 | 34.540 | 2.5946 | 2.9 |
| 24 | 37.021 | 2.4263 | 3.7 |

In some embodiments of the present invention, the crystal form A of the compound of formula (IV) has a differential scanning calorimetry (DSC) curve with an endothermic peak at 223.0° C.±3.0° C.

In some embodiments of the present invention, the DSC pattern of the crystal form A of the compound of formula (IV) is shown in FIG. 2.

In some embodiments of the present invention, the thermogravimetric analysis curve of the crystal form A of the compound of formula (IV) has a weight loss of 3.78% at 150.0° C.±3° C.

In some embodiments of the present invention, the crystal form A of the compound of formula (IV) has a TGA pattern as shown in FIG. 3.

The present invention also provides a preparation method of the crystal form A of the compound of formula (IV), which comprises adding any one of the forms of the compound of formula (IV) to an organic solvent containing ester or ether to prepare a slurry, wherein the temperature for preparing a slurry ranges from 20° C. to 40° C.

In some embodiments of the present invention, the ester is ethyl acetate, and the ether is methyl tert-butyl ether.

In some embodiments of the present invention, the time used to prepare a slurry ranges from 30 hours to 60 hours.

In some embodiments of the present invention, the weight-volume ratio of the compound of formula (IV) to the organic solvent is 1:5 to 40.

The present invention also provides a crystal form B of the compound of formula (IV), the X-ray powder diffraction pattern of which has characteristic diffraction peaks at the following 2θ angles: 11.27±0.2°, 21.44±0.2°, 22.32±0.2°.

In some aspects of the present invention, the crystal form B of the compound of formula (IV) has characteristic diffraction peaks in its X-ray powder diffraction pattern at the following 2θ angles: 11.27±0.20, 12.46±0.20, 18.44±0.28, 21.44±0.20, 22.3230.20, 25.51±0.20, 25.94±0.25, 26.49±0.20.

In some aspects of the present invention, the crystal form B of the compound of formula (IV) has characteristic diffraction peaks in its X-ray powder diffraction pattern at the following 2θ angles: 11.27±0.20, 12.46±0.20, 18.44±0.20, 20.03±0.20, 21.44±0.20, 22.32±0.20, 23.37±0.20, 24.19±0.20, 25.51±0.20, 25.94±0.20, 26.49±0.20, 28.12±0.20.

In some embodiments of the present invention, the XRPD pattern of the crystal form B of the compound of formula (IV) is shown in FIG. 4.

TABLE 2

XRPD pattern analysis data of crystal form B

| Number | 2θ angle (°) | Interplanar spacing (Å) | Relative strength (%) |
|---|---|---|---|
| 1 | 6.13 | 14.42 | 31.94 |
| 2 | 11.27 | 7.85 | 100.00 |
| 3 | 12.46 | 7.10 | 74.08 |
| 4 | 14.42 | 6.14 | 20.36 |
| 5 | 15.79 | 5.61 | 25.74 |
| 6 | 16.49 | 5.38 | 5.12 |
| 7 | 18.08 | 4.91 | 35.03 |
| 8 | 18.44 | 4.81 | 79.62 |
| 9 | 18.85 | 4.71 | 10.82 |
| 10 | 20.03 | 4.43 | 43.13 |
| 11 | 21.44 | 4.14 | 90.07 |
| 12 | 21.94 | 4.05 | 38.44 |
| 13 | 22.32 | 3.98 | 96.82 |
| 14 | 23.37 | 3.81 | 45.05 |
| 15 | 23.66 | 3.76 | 43.95 |
| 16 | 24.19 | 3.68 | 55.33 |
| 17 | 24.77 | 3.59 | 35.01 |
| 18 | 25.51 | 3.49 | 77.38 |
| 19 | 25.94 | 3.43 | 78.35 |
| 20 | 26.49 | 3.36 | 79.46 |
| 21 | 27.08 | 3.29 | 8.95 |
| 22 | 27.70 | 3.22 | 32.45 |
| 23 | 28.12 | 3.17 | 48.03 |
| 24 | 28.56 | 3.13 | 30.53 |
| 25 | 29.94 | 2.98 | 35.20 |
| 26 | 30.25 | 2.95 | 34.12 |
| 27 | 31.05 | 2.88 | 10.83 |
| 28 | 31.80 | 2.81 | 10.64 |
| 29 | 32.45 | 2.75 | 8.89 |
| 30 | 32.95 | 2.72 | 25.09 |
| 31 | 33.22 | 2.70 | 19.38 |
| 32 | 33.53 | 2.67 | 14.09 |
| 33 | 34.29 | 2.62 | 7.63 |
| 34 | 35.13 | 2.55 | 8.13 |
| 35 | 35.96 | 2.50 | 14.04 |
| 36 | 37.36 | 2.41 | 5.35 |

In some embodiments of the present invention, the crystal form B of the compound of formula (IV) has a differential scanning calorimetry (DSC) curve with an endothermic peak at 221.9° C.±3.0° C.

In some embodiments of the present invention, the DSC pattern of the crystal form B of the compound of formula (IV) is shown in FIG. 5.

In some embodiments of the present invention, the thermogravimetric analysis curve of the crystal form B of the compound of formula (IV) has a weight loss of 1.05% at 150.0° C.±3° C.

In some embodiments of the present invention, the crystal form B of the compound of formula (IV) has a TGA pattern as shown in FIG. 6.

The present invention also provides a method for preparing the crystal form B of the compound of formula (IV), which comprises adding any one of the forms of the compound of formula (IV) to ester, ether, alcohol, acetone, acetonitrile, n-heptane, water, a mixed organic solvent, and a mixture of water and organic solvent to prepare a slurry, wherein the temperature for preparing a slurry ranges from 40° C. to 60° C.

In some embodiments of the present invention, the method for preparing the crystal form B of the compound of formula (IV), wherein the ester is ethyl acetate, the ether is selected from the group consisting of tetrahydrofuran and methyl tert-butyl ether, the alcohol is ethanol. The mixed organic solvent is selected from the group consisting of a mixture of methyl tert-butyl ether and methanol with a volume ratio of 95:5, and a mixture of methyl tert-butyl ether and ethanol with a volume ratio of 95:5. The mixture of water and organic solvent is selected from the group consisting of a mixture of water and acetone with a volume ratio of 5:95, a mixture of water and acetonitrile with a volume ratio of 5:95, and a mixture of water and tetrahydrofuran with a volume ratio of 5:95.

In some embodiments of the present invention, the method for preparing the crystal form B of the compound of formula (IV), wherein the time used to prepare a slurry ranges from 30 hours to 60 hours.

In some embodiments of the present invention, the method for preparing the crystal form B of the compound of formula (IV), wherein the weight-volume ratio of the compound of formula (IV) to the mixed organic solvent ranges from 1:5 to 40.

The present invention also provides a use of the crystal form A or crystal form B in the manufacturing of drugs for treating SSAO-related diseases.

In some embodiments of the present invention, the SSAO-related disease is non-alcoholic steatohepatitis.

The present invention also provides a preparation method of the compound of formula (IV),

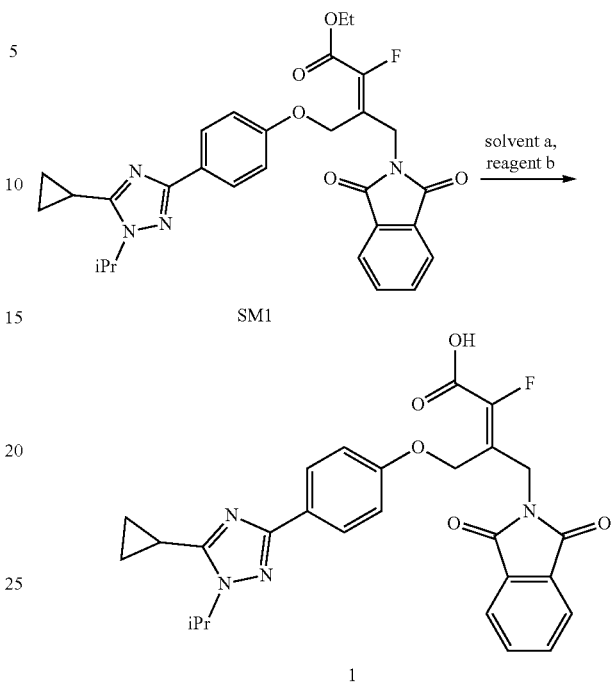

which comprises the following steps:

wherein, solvent a is acetic acid;

reagent b is hydrochloric acid.

In some embodiments of the present invention, in the preparation method of the compound of formula (IV), the volume-mass ratio of the solvent a to SM1 ranges from 3.0 to 3.5:1, and the volume-mass ratio of the reagent b to SM1 ranges from 3.0 to 10:1.

In some embodiments of the present invention, in the preparation method of the compound of formula (IV), wherein the internal temperature of the reaction is controlled to be at 75-80° C.

In some embodiments of the present invention, the preparation method of the compound of formula (IV) comprises the following steps:

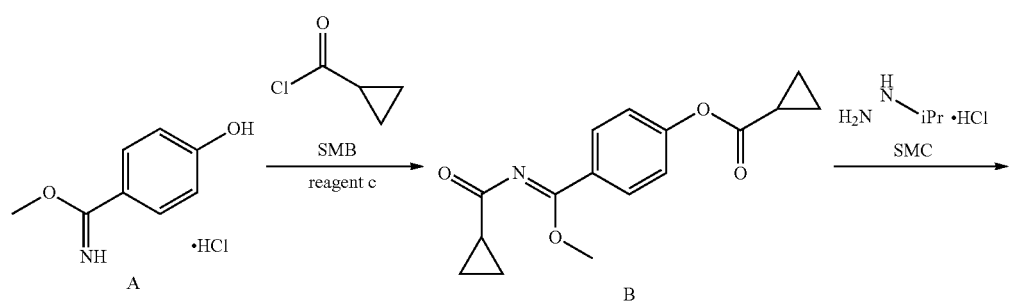

-continued
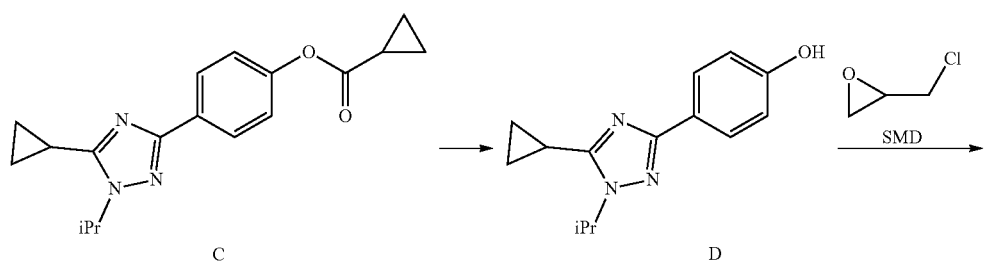
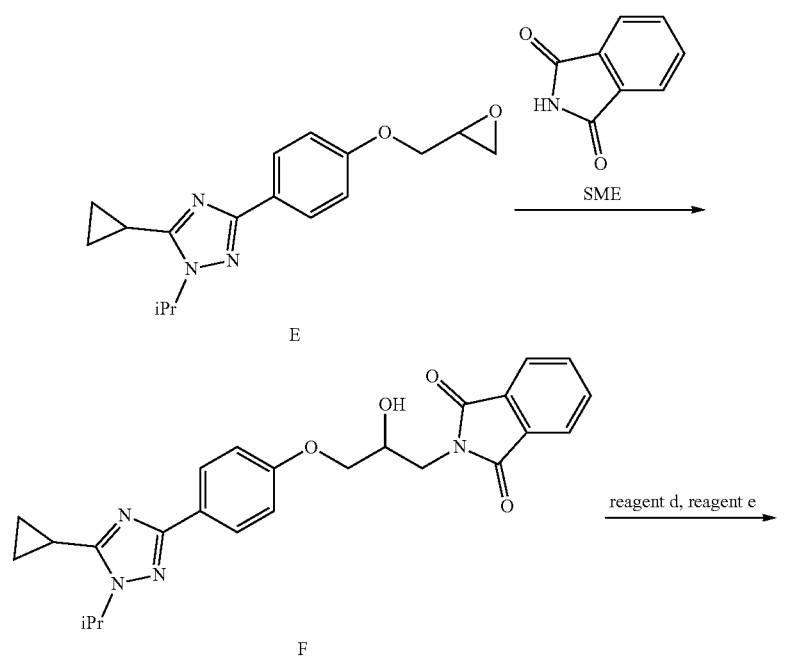
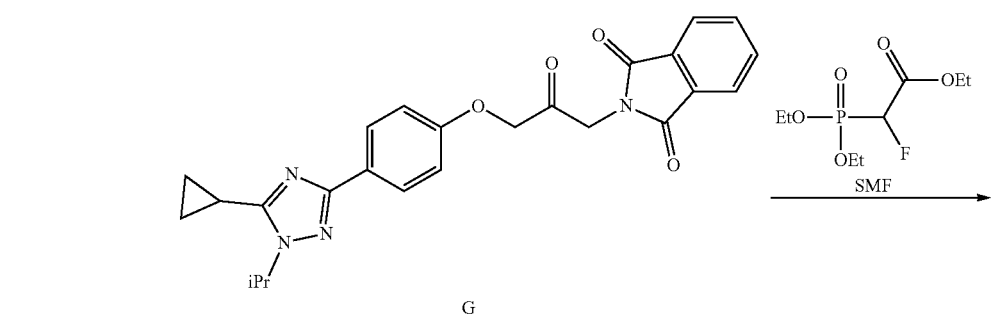
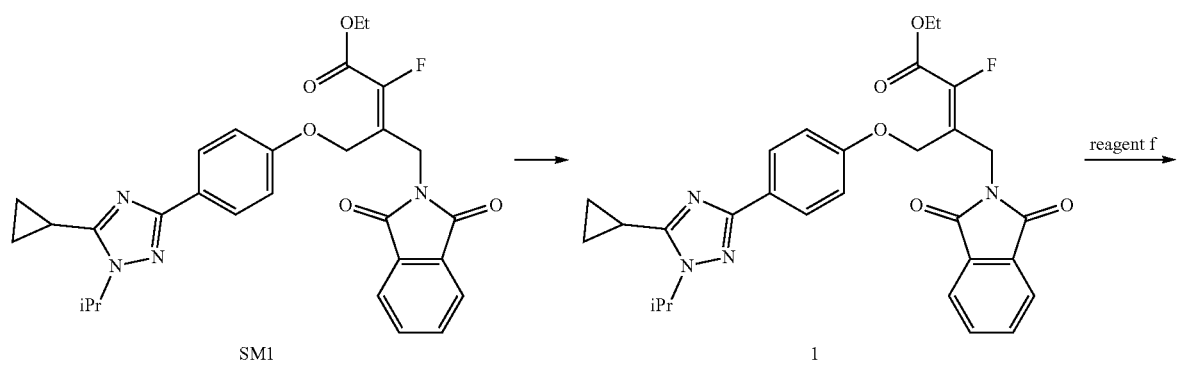

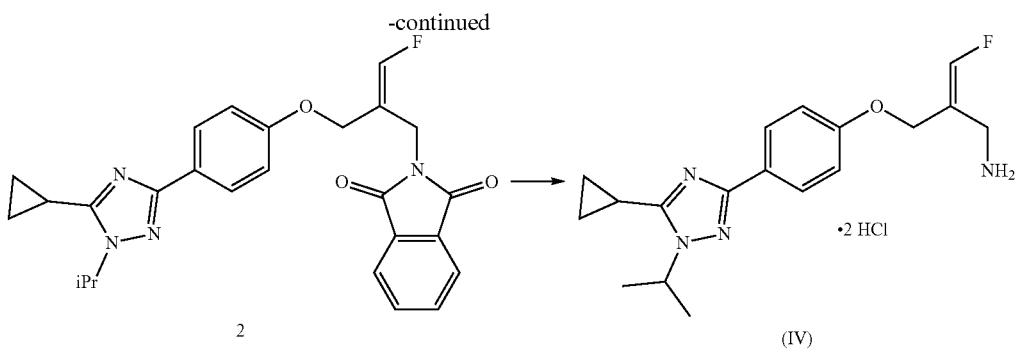

In some embodiments of the present invention, in the preparation method the compound of formula (IV), wherein reagent c is pyridine: the preparation of compound D is through a hydrolysis reaction under alkaline condition; reagent d is potassium bromide, and reagent e is sodium hypochlorite; reagent f is silver acetate.

Technical Effects

Crystal form A and crystal form B of the compound of formula (IV) of the present invention are of good stability. The compound of formula (IV) and crystal form B of the compound of formula (IV) showed strong inhibitory activity against human recombinant VAP-1/SSAO enzyme and against VAP-1/SSAO cell in in vitro assays.

Definitions and Descriptions

Unless otherwise specified, the following terms and phrases used herein are intended to have the following meanings. A specific phrase or term should not be considered uncertain or unclear without a special definition, but should be understood in its ordinary meaning. When a commercial name appears herein, it is intended to refer to its corresponding commercial product or its active ingredient.

The intermediate compounds of the present invention can be prepared by a variety of synthetic methods well known to those skilled in the art, including the specific embodiments listed below, the embodiments formed by combining them with other chemical synthesis methods, and the equivalent alternatives well-known by those skilled in the art. Preferred implementations include but are not limited to the embodiments of the present invention.

The chemical reactions in the specific embodiments of the present invention are completed in suitable solvents, and the solvents must be suitable for the chemical changes of the present invention and the required reagents and materials. In order to obtain the compounds of the present invention, it is sometimes necessary for those skilled in the art to modify or select the synthesis steps or reaction schemes based on the existing embodiments.

The present invention will be specifically described below through embodiments, and the protective scopes of the present invention are not limited thereby.

The structure of the compound of the present invention can be confirmed by conventional methods well known to those skilled in the art. If the present invention relates to the absolute configuration of the compound, the absolute configuration can be confirmed by conventional technical means in the field. For example, the single crystal X-ray diffraction method (SXRD), where the Bruker D8 venture diffractometer was used to collect the diffraction intensity data of the single crystal. The light source is CuKα radiation, and the scanning method is <p/w scanning. After collecting the relevant data, the direct method (Shelxs97) is further adopted to analyze the crystal's structure, and the absolute configuration of the compound can be confirmed thereby.

All solvents used in the present invention are commercially available and can be used without further purification.

The present invention uses the following acronyms: DMF represents dimethylformamide; DCM represents dichloromethane; DMSO represents dimethyl sulfoxide; MeOH represents methanol; MsOH represents methanesulfonic acid; EtOH represents ethanol; NaOH represents sodium hydroxide; TEA represents triethylamine; HCl represents hydrochloric acid; Tol represents toluene; KOH represents potassium hydroxide; TEBAC represents benzyl triethylammonium chloride; KBr represents potassium bromide; $NaHCO_3$ represents sodium bicarbonate; NaClO represents sodium hypochlorite; TEMPO represents 2,2,6,6-tetramethylpiperidine oxide; $Na_2S_2O_3$ represents sodium thiosulfate; AcOH represents acetic acid; NMP represents N-methyl pyrrolidone; AgOAc represents silver acetate; 2-MeTHF represents 2-methyltetrahydrofuran; DAST represents diethylaminosulfur trifluoride; TBSCl represents tert-butyldimethylchlorosilane; DMP represents dimethyl phthalate; NaHMDS represents sodium bis(trimethylsilyl)amide; TBAF represents tetrabutyl ammonium fluoride; MgEtBr represents ethyl magnesium bromide.

Compounds are named according to conventional naming principles or ChemDraw® software, and commercially available compounds use supplier catalog names.

X-Ray Powder Diffractometer (XRPD) Method in the Present Invention

Instrument model: Bruker D8 advance X-ray diffractometer

Test method: Approximately 10~ 20 mg sample used for XRPD detection

Detailed XRPD parameters are as follows:

Light tube: Cu, kα, (λ=1.54056 Å)

Light tube voltage: 40 kV, Light tube current: 40 mA

Divergence slit: 0.60 mm

Detector slit: 10.50 mm

Anti-scatter slit: 7.10 mm

Scan range: 4-40 deg

Step size: 0.02 deg

Step length: 0.12 seconds

Sample disk rotating speed: 15 rpm

The Differential Thermal Analysis (Differential Scanning Calorimeter, DSC) Method of the Present Invention Instrument model: TA Q2000 Differential Scanning Calorimeter Test method: the sample (about 1 mg) was placed in a DSC aluminum pan for testing. Under the condition of 50 mL/min $N_2$, at a heating rate of 10° C./min, the sample was heated from 30° C. (room temperature) to 300° C. (or 350° C.).

The Thermal Gravimetric Analysis (Thermal Gravimetric Analyzer, TGA) Method of the Present Invention Instrument model: TA Q5000IR thermogravimetric analyzer Test method: the sample (2-5 mg) was placed in a TGA platinum pot for testing. Under the condition of 25 mL/min $N_2$, at a heating rate of 10° C./min, the sample was heated from room temperature to 350° C. or to 20% weight loss.

X-Ray Single Crystal Diffraction Method of the Present Invention

Instrument model: Rigaku Oxford Diffraction XtaLAB Synergy-S

Test method: the sample was dissolved in 1 mL dichloromethane/methanol (1:1) at room temperature. The sample solution was placed in a 4 mL semi-sealed sample bottle and evaporated slowly at room temperature. Colorless bulk crystals were obtained the next day. Diffraction experiment temperature T=99.99(11) K.

Instrument Parameters:

Rigaku Oxford Diffraction XtaLAB Synergy four-circle diffractometer equipped with a HyPix-6000HE area detector.

Cryogenic system: Oxford Cryostream 800
Cu: λ=1.54184 Å, 50 W, Micro focus source with multilayer mirror (μ-CMF).
Distance from the crystal to the CCD detector: d=35 mm
Tube Voltage: 50 kV
Tube Current: 1 mA

DETAILED DESCRIPTION OF THE PREFERRED EMBODIMENTS

Figure 1:
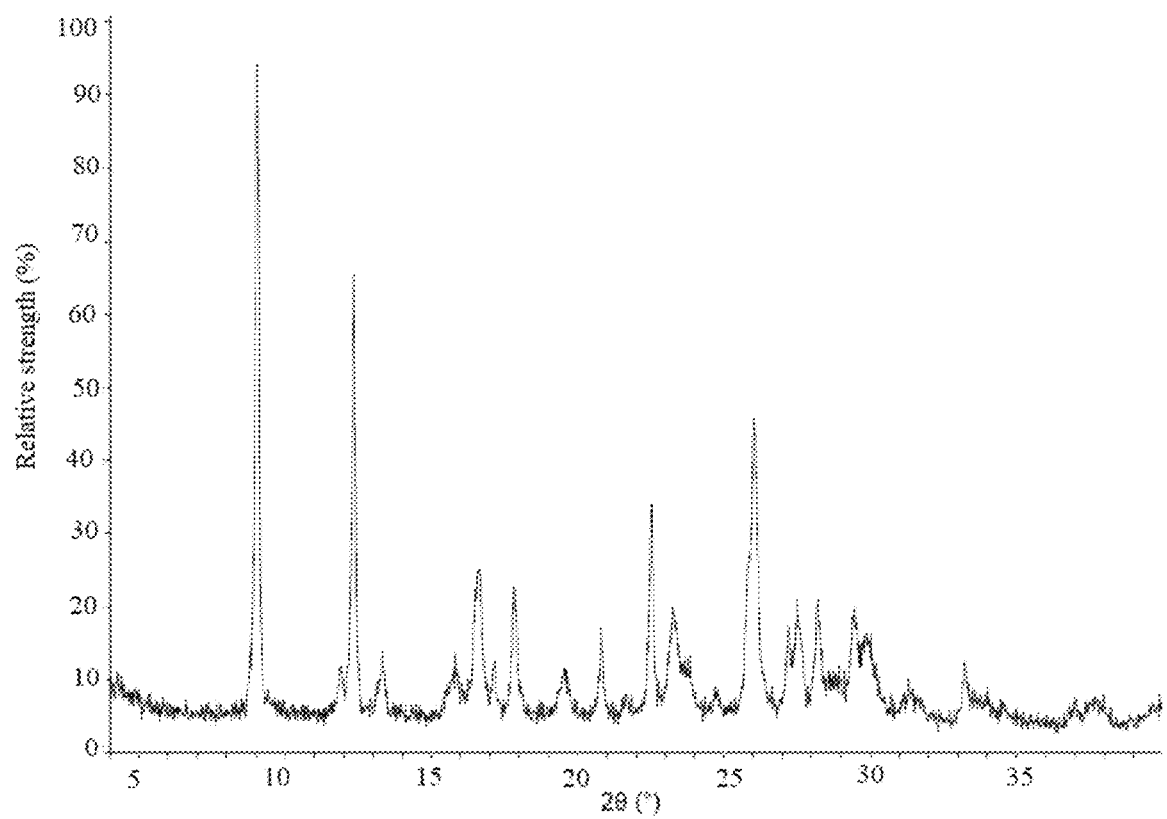
FIG. 1 is an XRPD spectrum of Cu-Kα radiation of the crystal form A of the compound of formula (IV).

In order to better understand the content of the present disclosure, the following specific examples are used for further description, but the specific embodiments do not limit the contents of the present invention thereto.

Example 1: Preparation of a Compound of Formula (IV)

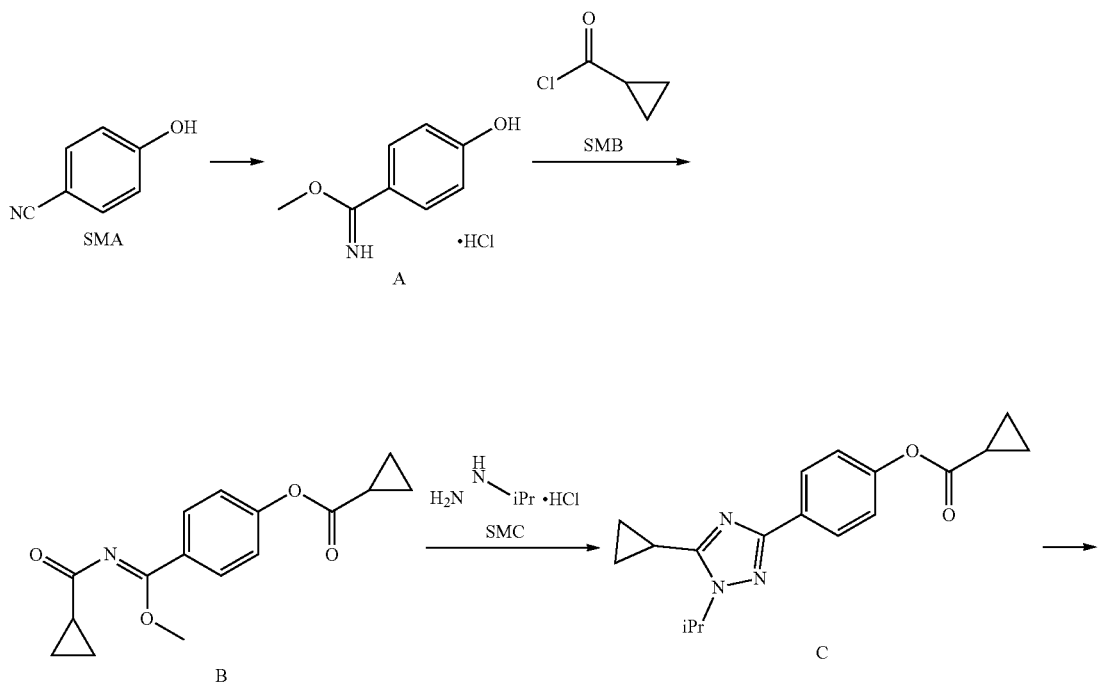

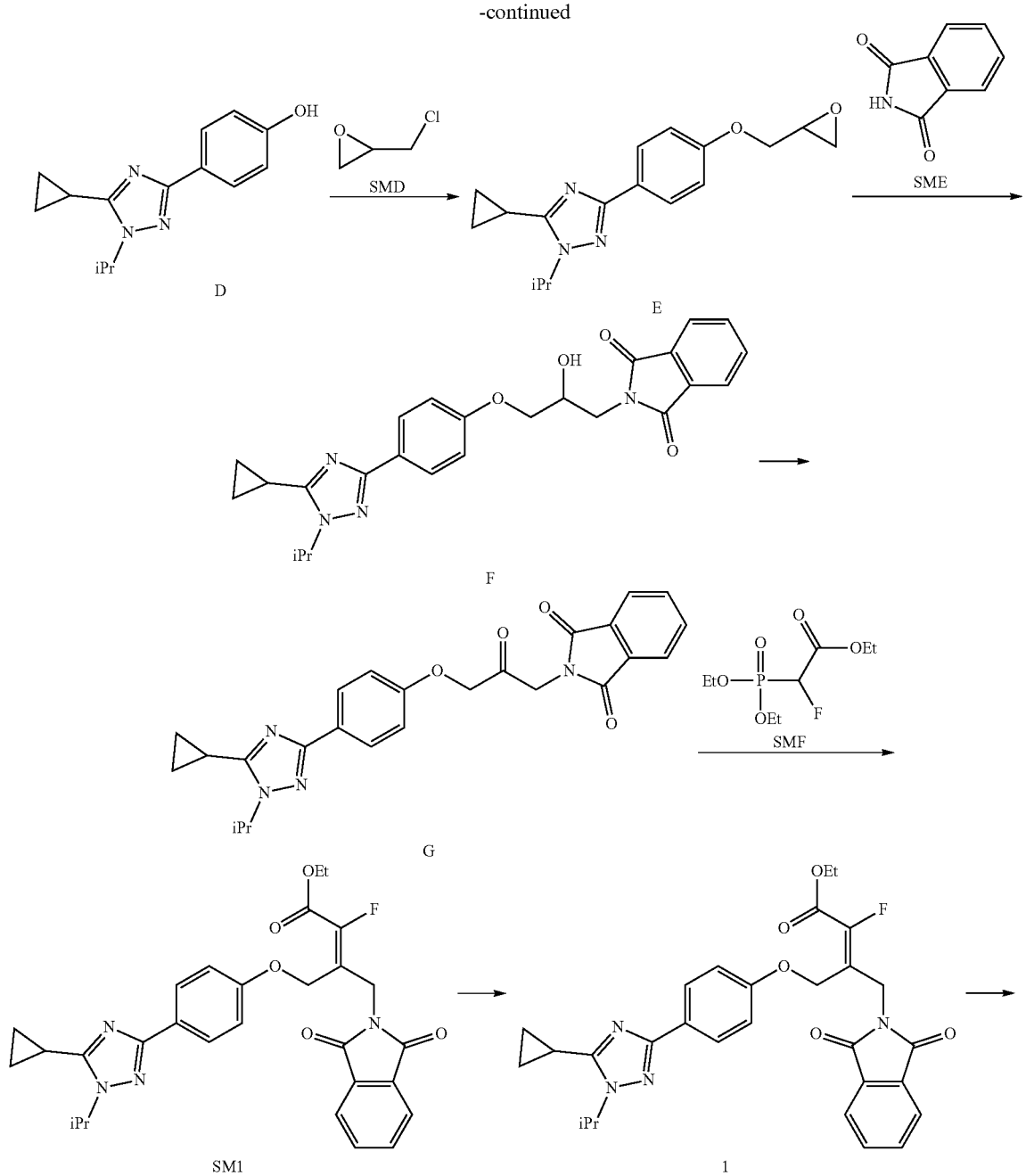
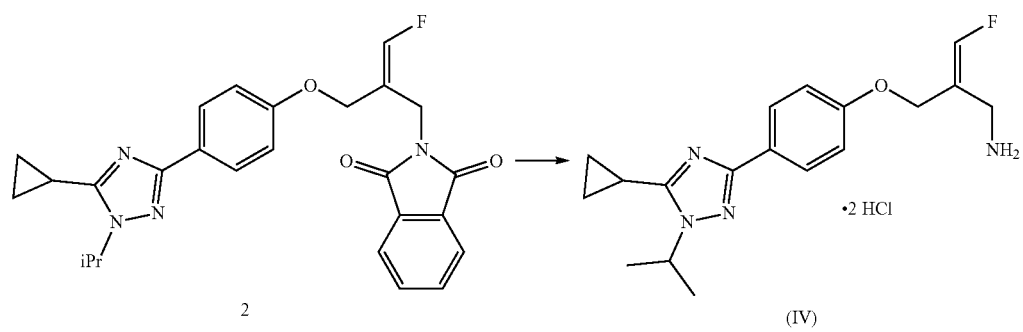

Step 1:

MeOH (2.5 L) was added to a clean and dry 50 L three-necked flask with stirring, and SMA (572 g, 4.80 mol) was added. In an ice-water bath, the temperature of the system was controlled at 0-30° C. Acetyl chloride (2.26 kg, 28.81 mol, 2.06 L) was slowly added to the system dropwise. At this stage, the heat was violently released. The dropping speed was carefully controlled. The addition was complete after 3 hours. After the addition, the ice-water bath was removed and the temperature of the system was controlled at 20-30° C. The reaction solution was stirred continuously for 16 hours. After the stirring was complete, the reaction solution was transferred to a desktop suction filter and filtered with suction, rinsed once with 1 L MeOH. The filter cake was collected and drained. The filter cake was transferred to a clean tray and left dry at room temperature for >24 hours. The material was collected to obtain compound A.

$^1$H NMR (399 MHz, DMSO-$d_6$) δ 11.18 (br s, 1H), 10.59-10.53 (m, 1H), 8.08-7.97 (m, 2H), 7.04-6.96 (m, 2H), 4.24 (s, 3H).

Step 2:

Compound A (500 g, 2.66 mol HCl) was dissolved in DCM (3 L). TEA (404.49 g, 4.00 mol, 556.39 mL) was added and the solution was stirred for 30 minutes. Then pyridine (421.59 g, 5.33 mol, 430.19 mL) was added to the above system. SMB (612.87 g, 5.86 mol, 532.93 mL) was added dropwise slowly and the temperature of the system was controlled at 10-30° C. The reaction was stirred at 20° C. for 1 hour. 1.5 L Water and 0.5M HCl (1.4 L) were added successively to adjust the pH of the system to 5-6. The aqueous phase was extracted with 1.5 L DCM once and the organic phases were combined. 4 L Water was added to wash the combined organic phase, and the organic phase was washed with 3 L saturated brine, partitioned. The organic phase was then dried over anhydrous sodium sulfate and concentrated under reduced pressure to obtain a crude product. The crude product was added to 2200 mL solvent (n-heptane:ethyl acetate=10:1) to slurry at 25° C. for 4 hours, and compound B was obtained after filtration.

$^1$H NMR (400 MHz, CDCl$_3$) δ 7.77-7.69 (m, 2H), 7.19-7.12 (m, 2H), 3.89 (s, 3H), 1.89-1.80 (m, 1H), 1.72-1.62 (m, 1H), 1.21-1.14 (m, 2H), 1.10-1.01 (m, 4H), 0.89 (qd, J=3.7, 7.7 Hz, 2H).

Step 3:

SMC (230.94 g, 2.09 mol) and toluene (3000 mL) were added to a dry three-necked flask. Then TEA (211.32 g, 2.09 mol, 290.67 mL, 1 eq) was added, the stirring was turned on, and the temperature was raised to an external temperature of 80° C.-90° C. (the internal temperature was stable at 72° C.). Compound B (600 g, 2.09 mol) was added in batches (the temperature was raised to 78° C. in half of the addition), and the temperature during the addition was controlled at 70-80° C. After the addition, the internal temperature was stabilized at 74° C., and the mixture was stirred for 2 hours. 2 L Water was added and the mixture was partitioned. The aqueous phase was extracted with ethyl acetate (1 L*2) and the organic phases were combined. The organic phase was washed with saturated brine (2 L*2) and separated. The organic phase was then dried over anhydrous sodium sulfate and concentrated under reduced pressure to obtain a crude product. The crude product was added to 2 L solvent (n-heptane:ethyl acetate=10:1) for slurrying at 25° C. for 2 hours. Compound C was obtained.

$^1$H NMR (400 MHz, DMSO-$d_6$) δ 7.93 (d, J=8.6 Hz, 2H), 7.17 (d, J=8.8 Hz, 2H), 4.90-4.77 (m, 1H), 2.22-2.12 (m, 1H), 1.95-1.83 (m, 1H), 1.46 (d, J=6.6 Hz, 6H), 1.04 (dtd, J=3.0, 5.0, 9.8 Hz, 6H), 1.00-0.96 (m, 2H).

Step 4:

In batches, EtOH (10 L) was added to a dry 50 L high-low temperature circulating bath, then compound C (3.3 kg, 10.6 mol) was added to the reaction kettle, and the stirring was turned on. The internal temperature was controlled at 0-40° C., and a mixed solution of NaOH (0.860 kg, 21.5 mol) and water (10 L) was added. The temperature was raised during the addition process but was not violent. After the addition, the reaction was stirred at 25-35° C. for 17-18 hours. The temperature of the reaction liquid was controlled, and 12 N HCl was added to the reaction liquid to adjust the pH to 3-4. Solid was precipitated. The reaction liquid was filtered in a desktop filter, and the filter cake was collected to obtain a crude product. Five batches of 20 kg crude products were combined and slurried with 2 volumes of acetonitrile at 25° C. for 1 hour. The mixture was filtered through a desktop filter, and the filter cake was rinsed with acetonitrile and then collected. Transfer the filter cake to a clean tray and leave to dry naturally for over 24 hours. Compound D was obtained.

$^1$H NMR (400 MHz, DMSO-$d_6$) δ 9.60 (s, 1H), 7.73 (d, J=8.7 Hz, 2H), 6.78 (d, J=8.5 Hz, 2H), 4.81 (quin, J=6.6 Hz, 1H), 2.20-2.09 (m, 1H), 1.44 (d, J=6.5 Hz, 6H), 1.09-1.00 (m, 2H), 0.98-0.92 (m, 2H).

Step 5:

Epichlorohydrin (6.600 kg) was added to a dry 50 L high-low temperature circulating bath. Then DMSO (6 L) was added, the stirring was turned on, and compound D (3.200 kg) was added. The remaining material was rinsed with DMSO (3 L). The internal temperature was controlled at 20-30° C., KOH (0.889 kg) was added, and the temperature was increased slightly. After the addition, the internal temperature was stabilized at 27-30° C., and the mixture was stirred for 18 hours. The reaction solution was discharged, and 8 L water was added to the reaction kettle, the stirring was turned on, the temperature was controlled at 0-30° C., and the reaction solution was slowly transferred to the reaction kettle through a peristaltic pump. Then 8 L methyl tert-butyl ether was added. The mixture was stirred for 15 minutes and kept for 15 minutes. The liquid was partitioned, and the organic phase was collected. The aqueous phase was then extracted again, and the organic phase was collected. The two organic phases were combined. Under stirring, 1 kg anhydrous sodium sulfate was added to the organic phase to dry the organic phase. The organic phase was concentrated under reduced pressure, and the temperature of the water bath was controlled to be less than 45° C. The pressure of the rotary vacuum was controlled to be less than −0.08 MPa for concentration. The oil pump was used to further reduce the pressure. The temperature of the water bath was controlled to <70° C., and the pressure of the rotary vacuum was <−0.08 Mpa. The organic phase was ultimately concentrated to 105% of the theoretical amount. The concentrated liquid was directly used in the next reaction. Compound E was obtained.

$^1$H NMR (399 MHz, DMSO-$d_6$) δ 7.88-7.80 (m, 2H), 6.99 (d, J=8.8 Hz, 2H), 4.83 (quin, J=6.6 Hz, 1H), 4.35 (dd, J=2.6, 11.4 Hz, 1H), 3.85 (dd, J=6.4, 11.2 Hz, 1H), 3.36-3.34 (m, 1H), 2.85 (t, J=4.6 Hz, 1H), 2.72 (dd, J=2.6, 4.8 Hz, 1H), 2.23-2.07 (m, 1H), 1.45 (d, J=6.6 Hz, 6H), 1.07-1.00 (m, 2H), 0.99-0.94 (m, 2H).

Step 6:

Compound E (3.86 kg) was dissolved in isopropanol (15 L), and the mixed solution was added to a dry 50 L high-low temperature circulating bath, and stirring was turned on. TEBAC (0.592 kg) and SME (2.295 kg) were added successively, and finally 5 L isopropanol was added to rinse the walls of the reaction kettle. The temperature was controlled at 80-90° C. and the reaction went on for 22 hours. 15 L n-Heptane was added to the reaction system, the stirring speed was reduced, the temperature was lowered slowly to 20-25° C., and the mixture was stirred for 1 hour to precipitate. A peristaltic pump was used to transfer the reaction solution to a desktop filter. The mixture was filtered with suction, and the filter cake was washed with 5 L n-heptane. Collect the filter cake and place on a clean tray, then leave to dry naturally for >24 hours. Compound F was obtained.

$^1$H NMR (400 MHz, DMSO-$d_6$) δ 7.90-7.83 (m, 4H), 7.81 (d, J=8.8 Hz, 2H), 6.90 (d, J=8.9 Hz, 2H), 5.40 (d, J=5.5 Hz, 1H), 4.88-4.75 (m, 1H), 4.25-4.11 (m, 1H), 3.99 (br s, 2H), 3.73 (s, 2H), 2.22-2.07 (m, 1H), 1.45 (d, J=6.7 Hz, 6H), 1.07-1.00 (m, 2H), 0.96 (br s, 2H).

Step 7:

Compound F (3.01 kg) was dissolved in DCM (15 L). The mixed solution was added to a dry high-low temperature circulating bath, and stirring was turned on. KBr (0.97 kg) was added, followed by a mixed solution of NaHCO$_3$ (2.83 kg) and H$_2$O (100 mL), and then TEMPO (54.00 g). The internal temperature was controlled to 0-5° C., and NaClO (16.4 kg, 6% mass content) was added dropwise. The temperature of the system was then controlled below 20-25° C. and the system was stirred for 2 hours. Stop the reaction and let stand still for 15 minutes. The liquid were partitioned, and the organic phase was collected. Saturated Na$_2$S$_2$O$_3$ (aq) (15 L) was added to wash the organic phase, and the mixture was stirred for 5 minutes, let stand still for 15 minutes, and the organic phase was separated. The organic phase was dried over anhydrous Na$_2$SO$_4$, filtered, and concentrated under reduced pressure. The temperature of the water bath was controlled to <45° C., and the pressure of the rotary vacuum was <−0.08 Mpa. The organic phase was concentrated until solid was precipitated. 5 L ethyl acetate was added, and the mixture was transferred to a 50 L spherical reaction kettle. 10 L n-heptane was added and the mixture was slurried for 16 hours. The solid was filtered off, and the filter cake was collected and placed on a clean tray and leave to dry naturally for >24 hours. Compound G was obtained.

$^1$H NMR (399 MHz, DMSO-$d_6$) δ 7.95-7.87 (m, 4H), 7.84 (d, J=8.8 Hz, 2H), 7.00 (d, J=8.8 Hz, 2H), 5.13 (s, 2H), 4.90-4.80 (m, 1H), 4.78 (s, 2H), 2.22-2.12 (m, 1H), 1.46 (d, J=6.6 Hz, 6H), 1.08-1.01 (m, 2H), 1.00-0.93 (m, 2H).

Step 8:

MgEtBr (3 M, 63.74 mL) was added to a solution of SMF (46.31 g, 191.23 mmol, 38.92 mL) in 2-MeTHF (200 mL) at 0° C., and the resultant reacted at 0-10° C. for 20 minutes, and compound G (50 g, 112.49 mmol) was added. After the addition was complete, the solution was heated to 40° C. and reacted for 1 hour. Saturated citric acid solution (200 mL) was added to the solution, and the solution was stirred for 10 minutes. The organic phase was separated and washed with 1M NaOH aqueous solution (200 mL). The mixture was stirred for 10 minutes, and the organic phase was separated. The organic phase was then dried by a rotary envaporator and slurried in 100 mL methyl tert-butyl ether:isopropanol=1:1 (2V) solvent at 25° C. for 16 hours, and the filter cake was collected by filtration. (The organic phase was directly dried by a rotary envaporator, and the product agglomerated by replacing a small amount of 2-MeTHF with isopropanol). SM1 was obtained.

$^1$H NMR (399 MHz, DMSO-$d_6$) δ 7.87-7.79 (m, 4H), 7.73 (d, J=8.8 Hz, 2H), 6.73 (d, J=9.2 Hz, 2H), 4.98 (d, J=0.9 Hz, 2H), 4.87-4.77 (m, 1H), 4.58 (d, J=2.6 Hz, 2H), 4.26 (q, J=7.0 Hz, 2H), 2.20-2.11 (m, 1H), 1.44 (d, J=6.6 Hz, 6H), 1.22 (t, J=7.0 Hz. 3H), 1.07-1.00 (m, 2H), 0.98-0.92 (m, 2H).

Step 9:

At 20-25° C., AcOH (8 L) was added to a dry and clean 50 L jacketed reactor. SM1 (2450 g, 4.60 mol) was added under stirring, and the system became a suspension system. Prepared 6 M HCl (8 L) solution was added to the system, and the system was heated up to 90-95° C. (the internal temperature was controlled at 75-80° C.). The above mixture reacted at 90-95° C. for 16 hours. The three-necked flask was transferred into 0° C. ice-water bath and the internal temperature was lowered to 0-10° C. The reaction system was transferred to a desktop filter for suction filtration to obtain a filter cake, and the filter cake was washed twice with water (2 L). The suction filtration continued until no filtrate was produced. AcOH (12 L) was added to the three-necked flask twice, the stirring was turned on, and the filter cake and the prepared 6 M HCl (12 L) solution were added. The solution was heated to 90-95° C. (the internal temperature was controlled at 75-80° C.). The solution reacted at 90-95° C. for 48 hours and was sampled. When the residual amount of SM1 was less than 2.0%, the reaction was stopped. The reaction solution was cooled to 0-10° C., filtered, and the filter cake was washed twice with 5 L water to obtain a crude product. The crude product was added to acetonitrile (8 L). The temperature was raised to 50-55° C., and the solution was stirred for 3 hours. The mixture was filtered while hot, and the filter cake was collected. The filter cake was placed in a fume hood at 25-30° C. to dry for 24 hours. Compound 1 was obtained.

$^1$H NMR (400 MHz, DMSO-$d_6$) δ 7.86-7.80 (m, 4H), 7.80-7.75 (m, 2H), 6.76 (d, J=8.8 Hz. 2H), 5.02 (s, 2H), 4.92-4.82 (m, 2H), 4.56 (d, J=2.4 Hz, 2H), 2.28-2.15 (m, 1H), 1.45 (d, J=6.5 Hz, 5H), 1.12-1.04 (m, 4H).

Step 10:

NMP (1.34 L) was added to a 5 L three-necked flask at 20-25° C., and compound 1 (1.34 kg, 2.66 mol) was added under stirring, the system became a suspension system and was heated to 135-140° C. (the internal temperature was controlled at 120-125° C.). AgOAc (433.98 g, 2.66 mol) was added to the previously mixed solution, and the resultant reacted at 135-140° C. (the internal temperature was controlled at 120-125° C.) for 16 hours. 0.2 eq AgOAc (88.80 g, 0.48 mol) was added and continue to maintain 135-140° C. (the internal temperature was controlled at 120-125° C.) until the reaction finished. The solution was cooled to 20-25° C. ethyl acetate (6.85 L) was added to the solution for dilution, activated carbon (543 g) and diatomaceous earth (543 g) were also added. The mixture was stirred for 20 minutes and then filtered through silica gel (543 g). The filter cake was washed three times with ethyl acetate (6.85 L). The filtrate was washed twice with 10% sodium thiosulfate solution (6.85 L), once with 0.5 M sodium hydroxide solution (6.85 L), and finally twice with water (6.85 L). The organic phase was dried under reduced pressure by a rotary envaporator to obtain the crude product. At 20-25° C., ethyl acetate (2.64 L) and n-heptane (13.2 L) were added into a 25 L drum, then the crude product (2.64 kg, 5.73 mol) was added. The mixture was slurried at 20-25° C. for 16 hours. The filter cake was collected by filtration to obtain compound 2.

$^1$H NMR (399 MHz, DMSO-$d_6$) δ 7.91-7.79 (m, 4H), 7.70 (d, J=8.8 Hz, 2H), 7.38-7.08 (m, 1H), 6.73-6.65 (m,

2H), 4.82 (quin, J=6.6 Hz, 1H), 4.49-4.38 (m, 4H), 2.21-2.09 (m, 1H), 1.44 (d, J=6.6 Hz, 6H), 1.06-1.00 (m, 2H), 0.97-0.91 (m, 2H).

Step 11:

2-MeTHF solution (6 L) was added to a 50 L high-low temperature jacketed kettle at 20-25° C. Compound 2 (2 kg, 4.343 mol) was added with stirring. Water (3 L) and ethanolamine (2.652 kg, 43.43 mol) were added when the system was totally dissolved. The system was heated to 75-80° C. (the internal temperature was controlled at 65-70° C.) and reacted at 75-80° C. (the internal temperature was controlled at 65-70° C.) for 16 hours. The reaction solution was cooled to 20-25° C., then the liquid was partitioned, and the organic phase was collected. The aqueous phase was extracted once with 2-MeTHF solution (6 L); the organic phases were combined and dried under reduced pressure. The crude product was dissolved in 3 N hydrochloric acid (6 L), and the aqueous solution was extracted once with methyl tert-butyl ether (6 L) and twice with ethyl acetate (6 L). The pH of the aqueous solution was adjusted to above 10 with 1M sodium hydroxide solution. The aqueous solution was extracted twice with methyl tert-butyl ether (6 L), and the organic phases were combined. The insoluble matter was filtered off from the organic phase, and the organic phase was dried under reduced pressure by rotary evaporator. The organic phase was then dissolved in 2-MeTHF solution (6 L), washed once with 0.5 M sodium hydroxide solution (6 L) and twice with water (6 L). The organic phase was collected and dried under reduced pressure by rotary evaporator. The crude product was added to a 5 L single-neck flask, then ethyl acetate (2.86 L) and isopropanol (2.86 L) were added. The external temperature was controlled at 70-75° C., and the mixture was stirred and dissolved for 10 minutes. The above mixture was filtered while hot, and the insoluble matter was removed. The filtrate was collected. At 70-75° C., ethyl acetate (1.43 L) and isopropanol (1.43 L) were added and isopropanol hydrochloride solution (1.086 L) was added dropwise to the filtrate. After the addition, the mixture was cooled down to 50-55° C. and reacted at 50-55° C. for 2 hours. When the reaction finished, the solution was cooled to 20-25° C. and filtered. The filter cake was washed twice with ethyl acetate (1.43 L) to obtain a crude product. The crude product solid and ethyl acetate (4.29 L) were added to a 3 L single three-neck flask at 20-25° C., and the mixture was stirred at 20-25° C. for 16 hours, filtered to obtain the solid. The solid, ethyl acetate (2.15 L) and methanol (2.15 L) were added to a 3 L three-necked flask at 20-25° C. and stirred at 20-25° C. for 16 hours. The compound of formula (IV) was obtained by filtration.

$^1$H NMR (400 MHz, DMSO-$d_6$) δ 8.46 (br s, 3H), 8.00 (d, J=8.8 Hz, 2H), 7.47-7.19 (m, 1H), 7.10 (d, J=8.9 Hz, 2H), 4.92 (td, J=6.6, 13.1 Hz, 1H), 4.71 (d, J=3.1 Hz, 2H), 3.59 (br d, J=4.6 Hz, 2H), 2.36-2.26 (m, 1H), 1.47 (d, J=6.5 Hz, 5H), 1.22 (br d, J=2.6 Hz, 2H), 1.17-1.09 (m, 2H)

Example 2: Single Crystal X-Ray Diffraction Analysis of the Compound of Formula (IV)

Figure 7:
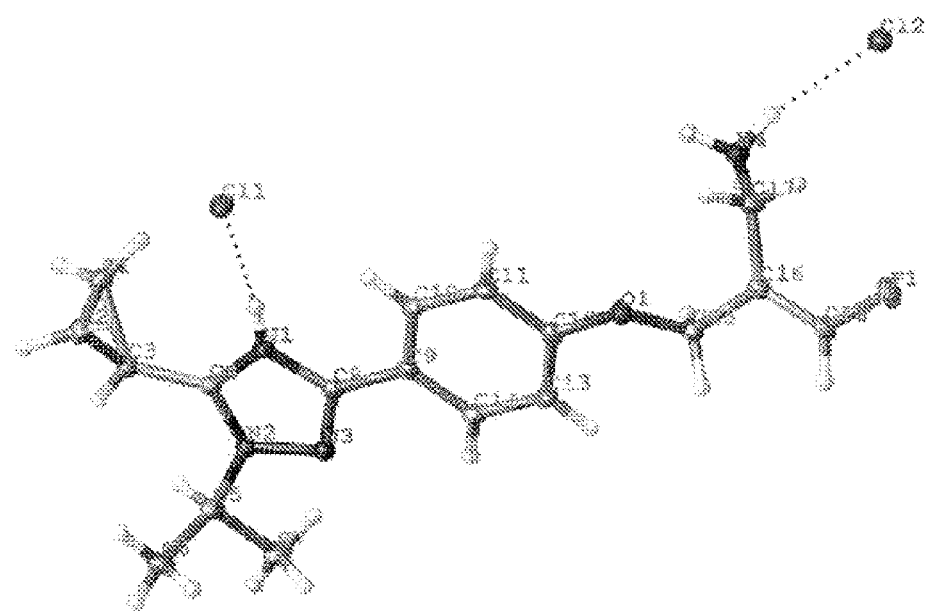
FIG. 7 is an ellipsoid diagram of the three-dimensional structure of the compound of formula (IV).
Figure 1:
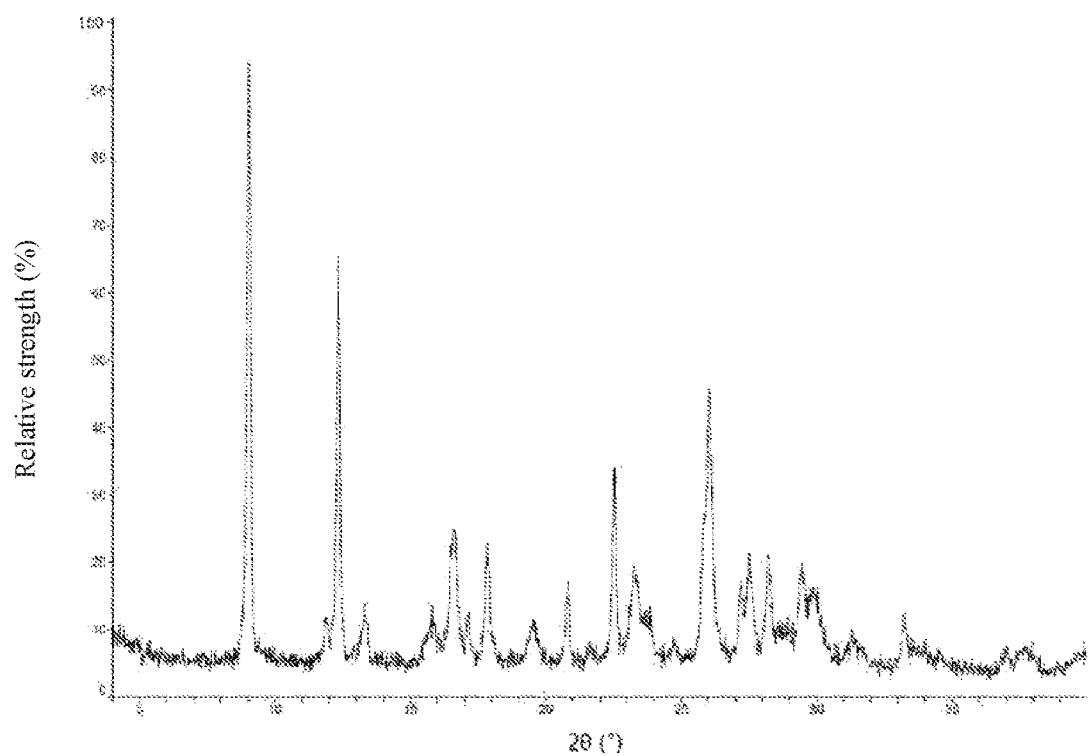
Figure 2:
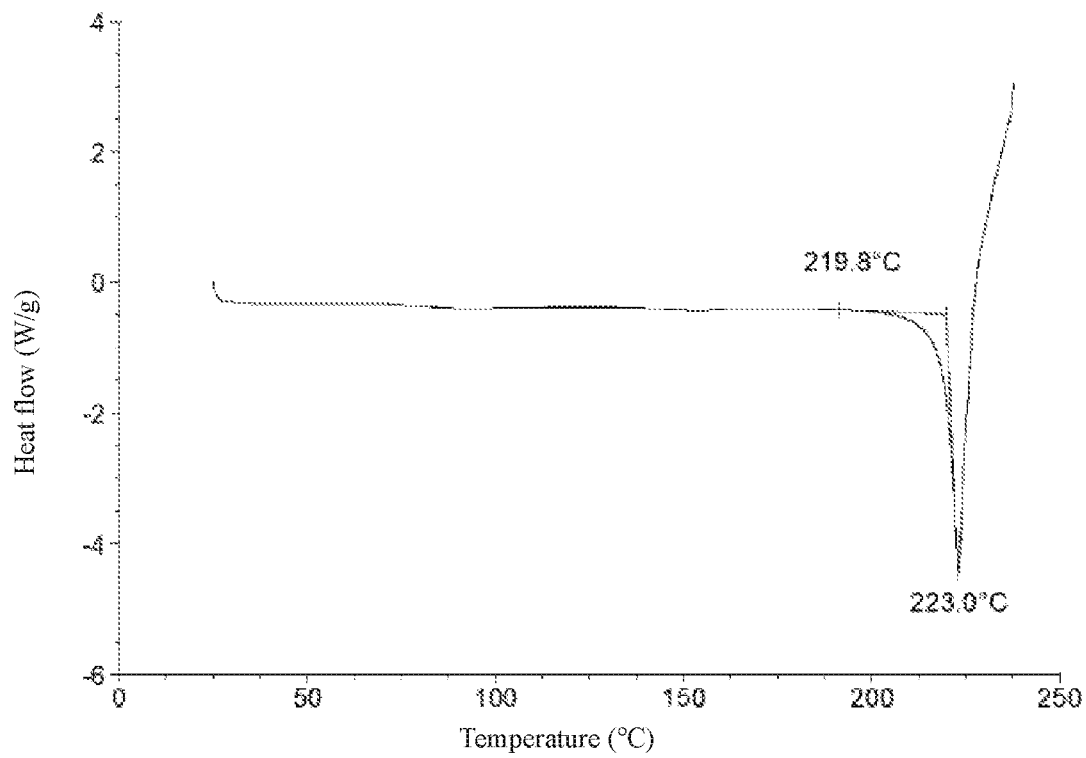
Figure 3:
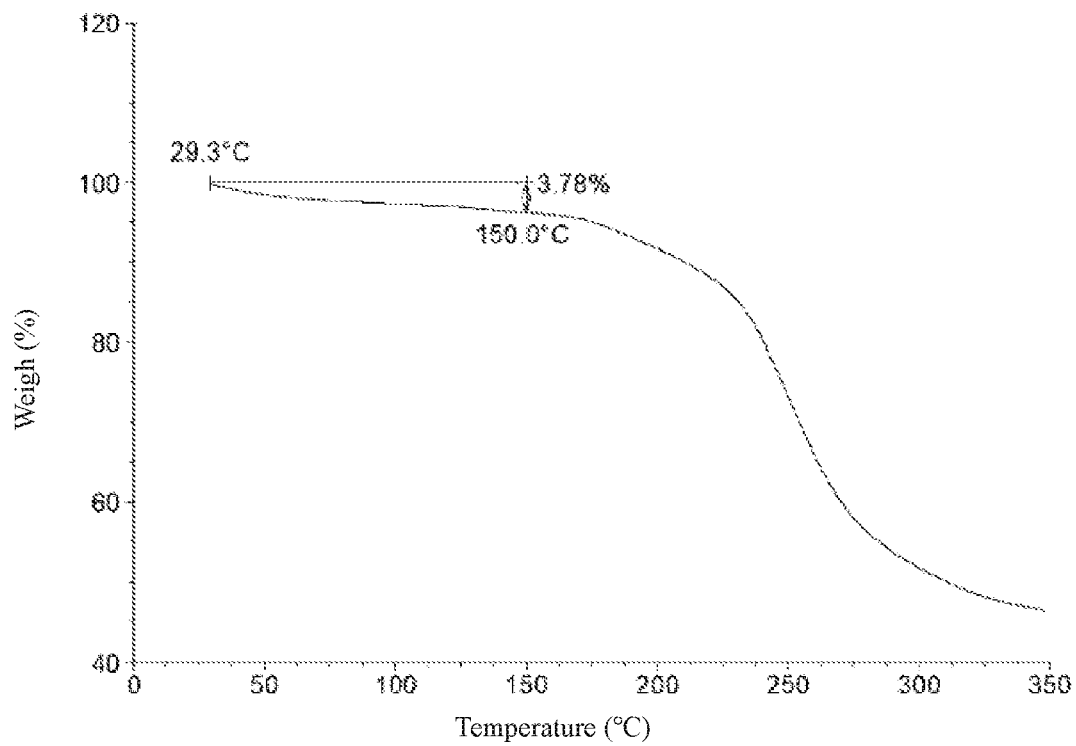
Figure 4:
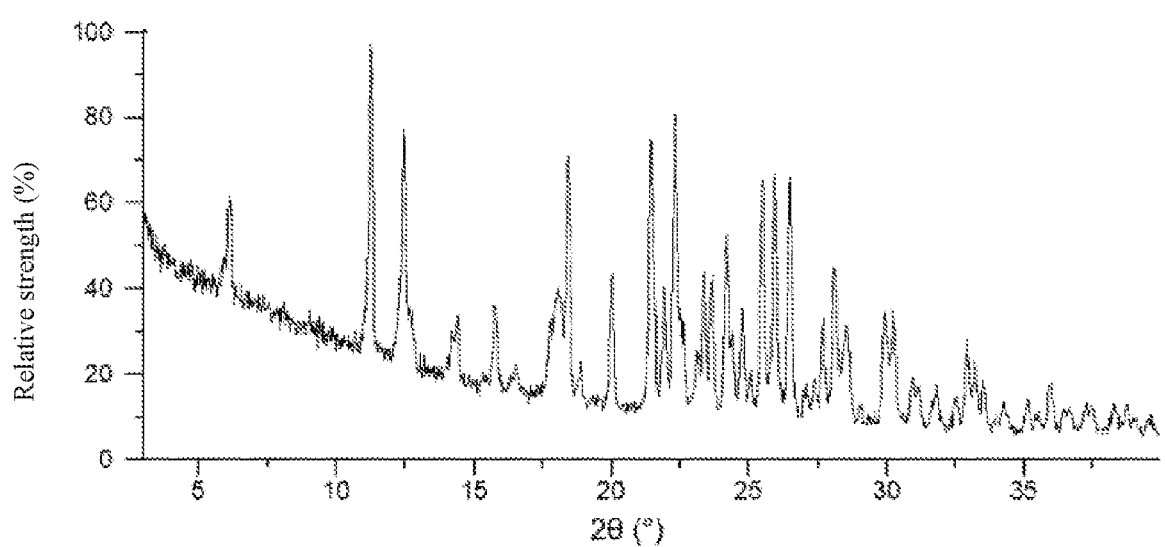
Figure 5:
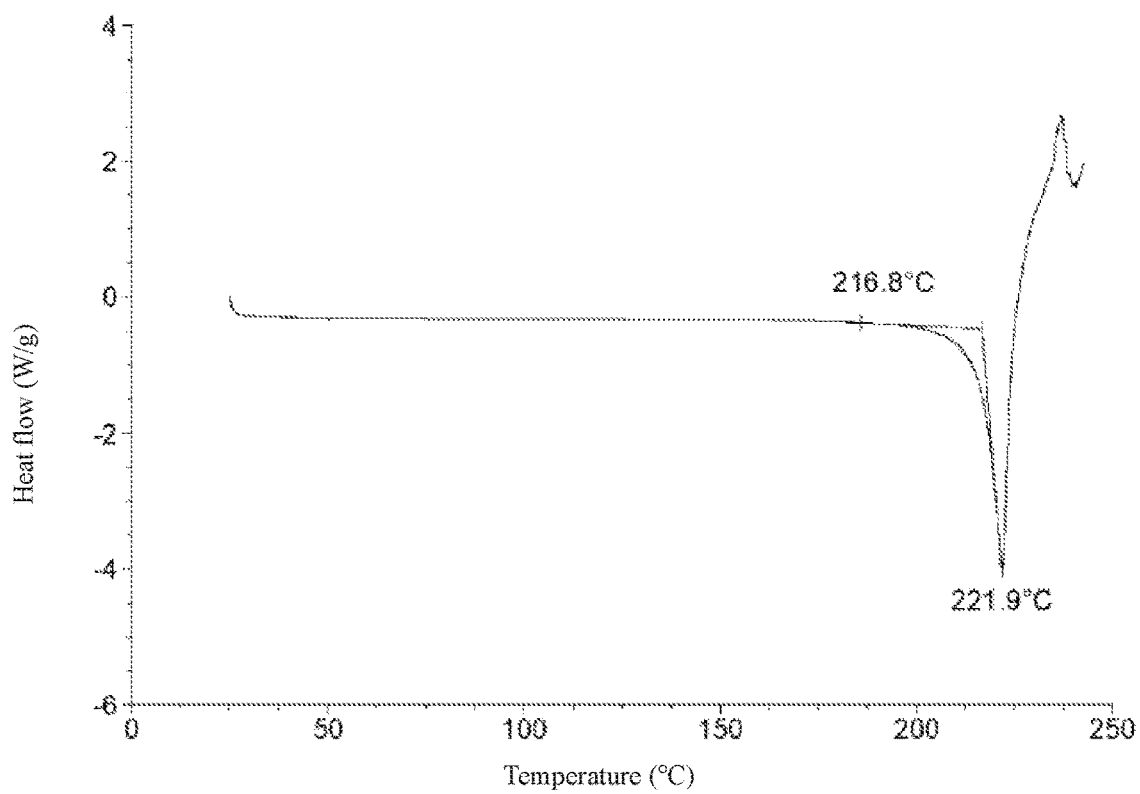
Figure 6:
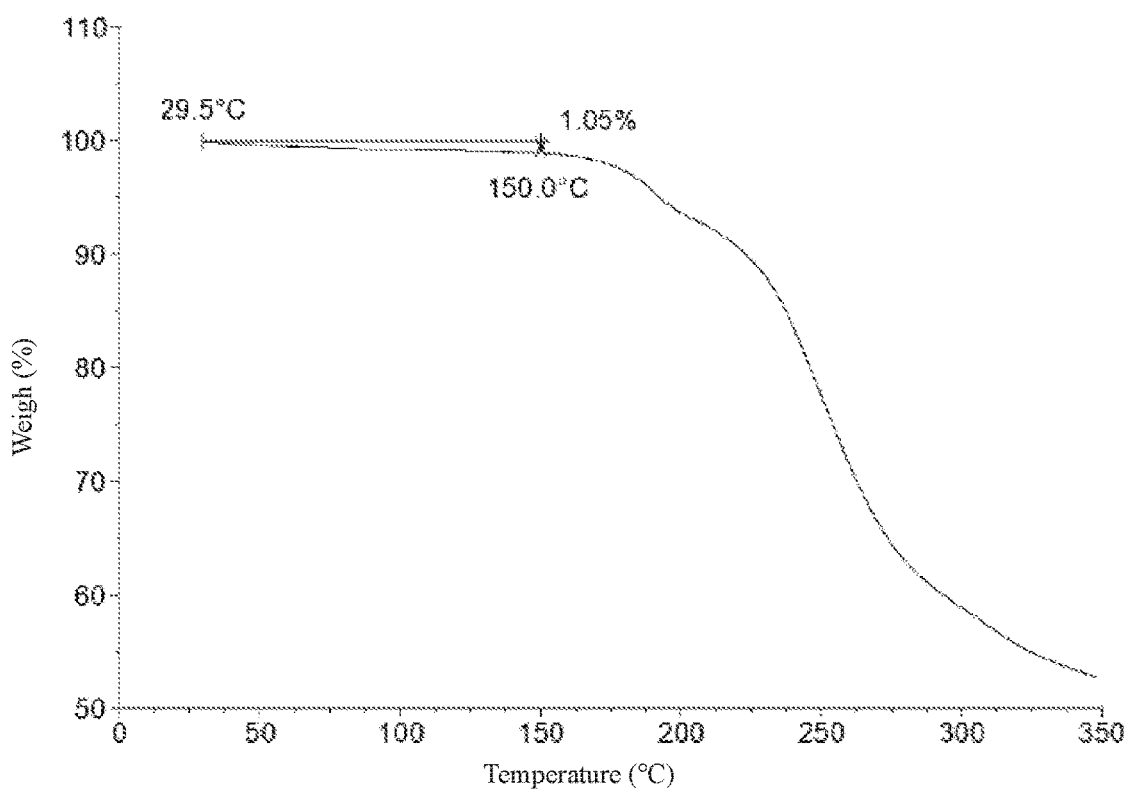
Figure 7:
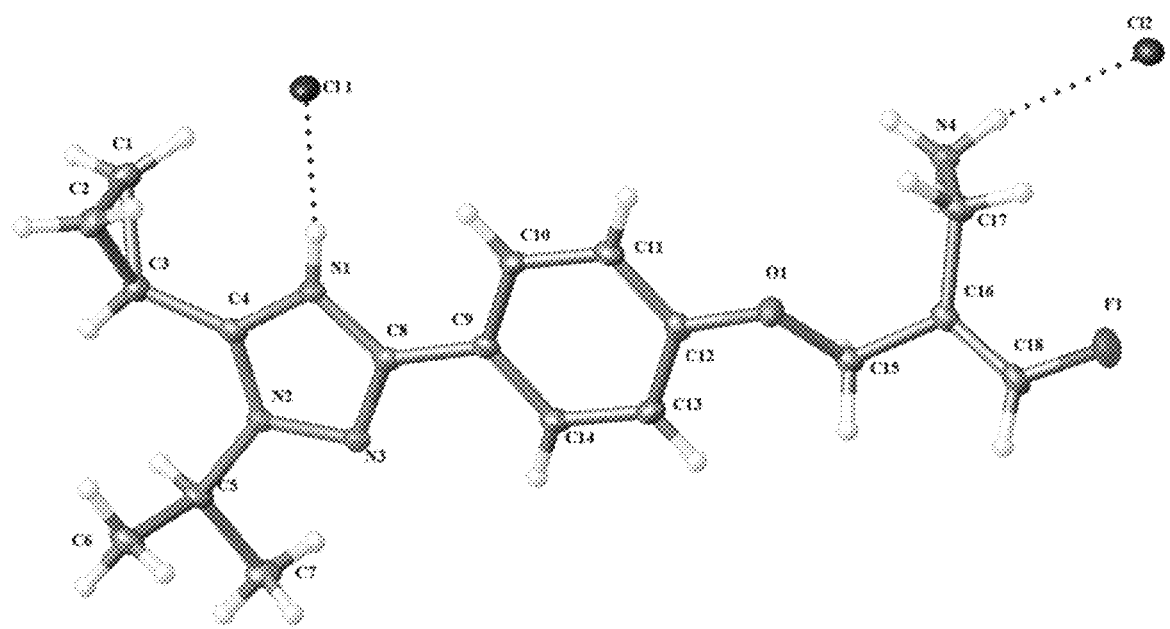

Single crystal preparation process: the sample was dissolved in 1 ml dichloromethane/methanol (1:1) at room temperature. The sample solution was placed in a 4 ml semi-sealed sample bottle and evaporated slowly at room temperature. Colorless bulk crystals were obtained the next day. The ellipsoid diagram of the three-dimensional structure of the compound of formula (IV) is shown in FIG. 7. The crystal structure data and parameters of the compound of formula (I) were shown in Tables 3, 4, 5, 6 and 7.

TABLE 3

Crystal data of the compound of formula (IV)

| | |
|---|---|
| Crystal Size | 0.20 × 0.10 × 0.04 mm$^3$ |
| Radiation Type | Cu Kα (λ = 1.54184Å) |
| Crystal system | monoclinic |
| Space Group | P2$_1$/n |
| Cell Size | a = 8.28140(10) Å |
| | b = 28.8396(3) Å |
| | c = 8.53030(10) Å |
| | α = 90° |
| | β = 107.9200(10)° |
| | γ = 90° |
| Cell Volume | V = 1938.47(4) Å$^3$ |
| Cell Formula Units | Z = 4 |
| Crystal Density | D$_c$ = 1.382 Mg/m$^3$ |
| Crystal F(000) | 848.0 |
| Absorption Coefficient mu | μ(Cu Kα)= 3.221 mm$^{-1}$ |
| Limiting Indices | −9 ≤ h ≤ 9 |
| | −34 ≤ k ≤ 34 |
| | −10 ≤ l ≤ 8 |
| Cell Measurement Temperature | T = 99.99 (11) K. |
| 2θ range for data collection | 6.13 to 133.198° |
| Goodness-of-fit on F^2 | 1.103 |
| Final R indices [I > 2sigma(I)] | R$_1$ = 0.0471, wR$_2$ = 0.1179 |
| R indices (all data) | R$_1$ = 0.0494, wR$_2$ = 0.1198 |
| Largest diff. peak and hole | 0.59 and —0.37 e.Å$^{-3}$ |
| Reflections collected/unique | 69088/3421 [R$_{(int)}$ = 0.0898] |

TABLE 4

Atomic coordinates (×10$^4$) and equivalent isotropic shift parameters (Å$^2$ × 10$^3$) of the crystal of compound of formula (IV)

| | x | y | z | U(eq) |
|---|---|---|---|---|
| Cl(2) | 7011.4(8) | 7783.5(2) | 13110.2(7) | 18.93(17) |
| F(1) | 8152(2) | 7832.6(5) | 8261(2) | 27.2(4) |
| O(1) | 6213(2) | 6329.9(6) | 7217(2) | 19.0(4) |
| N(1) | 1869(3) | 4411.7(7) | 5275(3) | 14.9(4) |
| N(2) | −12(3) | 4419.0(7) | 2907(3) | 15.2(4) |
| N(3) | 760(3) | 4846.1(7) | 3072(3) | 15.4(4) |
| N(4) | 5759(3) | 7011.9(8) | 10443(3) | 19.1(5) |
| C(8) | 1911(3) | 4832.0(8) | 4533(3) | 14.2(5) |
| C(11) | 5379(3) | 5556.7(9) | 7373(3) | 16.7(5) |
| C(9) | 3049(3) | 5217.9(9) | 5234(3) | 14.3(5) |
| C(4) | 648(3) | 4155.3(9) | 4232(3) | 15.6(5) |
| C(10) | 4336(3) | 5180.4(9) | 6741(3) | 16.0(5) |
| C(16) | 6696(3) | 7127.8(9) | 7944(3) | 16.7(5) |
| C(12) | 5143(3) | 5973.7(9) | 6509(3) | 15.5(5) |
| C(13) | 3889(3) | 6010.2(9) | 4989(3) | 18.7(5) |
| C(18) | 7188(3) | 7495.3(9) | 7302(3) | 20.0(6) |
| C(15) | 5541(3) | 6789.7(9) | 6784(3) | 16.9(5) |
| C(14) | 2852(3) | 5633.9(9) | 4367(3) | 17.7(5) |
| C(5) | −1357(3) | 4990.5(9) | 1366(3) | 17.0(5) |
| C(3) | 135(3) | 3685.4(9) | 4456(3) | 18.2(5) |
| C(1) | 212(4) | 3510.1(9) | 6155(3) | 21.9(6) |
| C(2) | 1447(4) | 3332.1(9) | 5351(3) | 21.2(6) |
| C(17) | 7227(3) | 7033.8(10) | 9762(3) | 20.7(6) |
| C(7) | −2110(3) | 4722.7(10) | 395(3) | 21.9(6) |
| C(6) | −633(4) | 3958(1) | 362(3) | 24.4(6) |
| Cl(1) | 4148.9(9) | 4026.1(2) | 8556.6(8) | 23.69(18) |

TABLE 5

Bond length (Å) of the compound of formula (IV)

| | Bond length/Å | | Bond length/Å |
|---|---|---|---|
| F(1)—C(18) | 1.360(3) | C(9)—C(10) | 1.398(4) |
| O(1)—C(12) | 1.370(3) | C(9)—C(14) | 1.393(4) |
| O(1)—C(15) | 1.442(3) | C(4)—C(3) | 1.450(4) |
| N(1)—C(8) | 1.373(3) | C(16)—C(18) | 1.314(4) |
| N(1)—C(4) | 1.344(3) | C(16)—C(15) | 1.504(3) |
| N(2)—N(3) | 1.375(3) | C(16)—C(17) | 1.500(4) |
| N(2)—C(4) | 1.332(3) | C(12)—C(13) | 1.393(4) |

TABLE 5-continued

Bond length (Å) of the compound of formula (IV)

| | Bond length/Å | | Bond length/Å |
|---|---|---|---|
| N(2)—C(5) | 1.485(3) | C(13)—C(14) | 1.384(4) |
| N(3)—C(8) | 1.316(3) | C(5)—C(7) | 1.520(4) |
| N(4)—C(17) | 1.501(3) | C(5)—C(6) | 1.526(4) |
| C(8)—C(9) | 1.462(3) | C(3)—C(1) | 1.518(4) |

TABLE 5-continued

Bond length (Å) of the compound of formula (IV)

| | Bond length/Å | | Bond length/Å |
|---|---|---|---|
| C(11)—C(10) | 1.389(4) | C(3)—C(2) | 1.514(4) |
| C(11)—C(12) | 1.393(4) | C(1)—C(2) | 1.487(4) |

TABLE 6

Bond angle (°) of the compound of formula (IV)

| | Bond angle/° | | Bond angle/° |
|---|---|---|---|
| C(12)—O(1)—C(15) | 115.50(19) | C(18)—C(16)—C(17) | 123.1(2) |
| C(4)—N(1)—C(8) | 107.5(2) | C(17)—C(16)—C(15) | 119.2(2) |
| N(3)—N(2)—C(5) | 120.82(19) | O(1)—C(12)—C(11) | 116.6(2) |
| C(4)—N(2)—N(3) | 111.6(2) | O(1)—C(12)—C(13) | 123.4(2) |
| C(4)—N(2)—C(5) | 127.5(2) | C(11)—C(12)—C(13) | 120.1(2) |
| C(8)—N(3)—N(2) | 104.3(2) | C(14)—C(13)—C(12) | 119.6(2) |
| N(1)—C(8)—C(9) | 126.0(2) | C(16)—C(18)—F(1) | 121.7(2) |
| N(3)—C(8)—N(1) | 110.5(2) | O(1)—C(15)—C(16) | 108.1(2) |
| N(3)—C(8)—C(9) | 123.5(2) | C(13)—C(14)—C(9) | 120.9(2) |
| C(10)—C(11)—C(12) | 120.0(2) | N(2)—C(5)—C(7) | 110.4(2) |
| C(10)—C(9)—C(8) | 122.0(2) | N(2)—C(5)—C(6) | 109.7(2) |
| C(14)—C(9)—C(8) | 118.9(2) | C(7)—C(5)—C(6) | 112.1(2) |
| C(14)—C(9)—C(10) | 119.1(2) | C(4)—C(3)—C(1) | 120.6(2) |
| N(1)—C(4)—C(3) | 128.2(2) | C(4)—C(3)—C(2) | 120.1(2) |
| N(2)—C(4)—N(1) | 106.1(2) | C(2)—C(3)—C(1) | 58.73(17) |
| N(2)—C(4)—C(3) | 125.8(2) | C(2)—C(1)—C(3) | 60.51(17) |
| C(11)—C(10)—C(9) | 120.2(2) | C(1)—C(2)—C(3) | 60.75(18) |
| C(18)C(16)—C(15) | 117.7(2) | C(16)—C(17)—N(4) | 113.2(2) |

TABLE 7

Torsion angle (°) of the compound of formula (IV)

| | Torsion angle/° | | Torsion angle/° |
|---|---|---|---|
| O(1)—C(12)—C(13)—C(14) | −179.5(2) | C(4)—N(2)—C(5)—C(7) | 163.0(2) |
| N(1)—C(8)—C(9)—C(10) | 4.8(4) | C(4)—N(2)—C(5)—C(6) | −73.1(3) |
| N(1)—C(8)—C(9)—C(14) | −175.7(2) | C(4)—C(3)—C(1)—C(2) | −108.8(3) |
| N(1)—C(4)—C(3)—C(1) | 33.3(4) | C(4)—C(3)—C(2)—C(1) | 109.6(3) |
| N(1)—C(4)—C(3)—C(2) | −35.9(4) | C(10)—C(11)—C(12)—O(1) | 179.5(2) |
| N(2)—N(3)—C(8)—N(1) | −0.2(3) | C(10)—C(11)—C(12)—C(13) | −1.6(4) |
| N(2)—N(3)—C(8)—C(9) | −179.9(2) | C(10)—C(9)—C(14)—C(13) | −1.1(4) |
| N(2)—C(4)—C(3)—C(1) | −147.4(3) | C(12)—O(1)—C(15)—C(16) | 167.3(2) |
| N(2)—C(4)—C(3)—C(2) | 143.3(3) | C(12)—C(11)—C(10)—C(9) | 0.1(4) |
| N(3)—N(2)—C(4)—N(1) | −0.1(3) | C(12)—C(13)—C(14)—C(9) | −0.3(4) |
| N(3)—N(2)—C(4)—C(3) | −179.5(2) | C(18)—C(16)—C(15)—O(1) | 131.7(2) |
| N(3)—N(2)—C(5)—C(7) | −19.8(3) | C(18)—C(16)—C(17)—N(4) | 118.9(3) |
| N(3)—N(2)—C(5)—C(6) | 104.1(3) | C(15)—O(1)—C(12)—C(11) | −152.8(2) |
| N(3)—C(8)—C(9)—C(10) | −175.5(2) | C(15)—O(1)—C(12)—C(13) | 28.4(3) |
| N(3)—C(8)—C(9)—C(14) | 4.0(4) | C(15)—C(16)—C(18)—F(1) | 176.2(2) |
| C(8)—N(1)—C(4)—N(2) | 0.0(3) | C(15)—C(16)—C(17)—N(4) | −60.9(3) |
| C(8)—N(1)—C(4)—C(3) | 179.4(2) | C(14)—C(9)—C(10)—C(11) | 1.2(4) |
| C(8)—C(9)—C(10)—C(11) | −179.3(2) | C(5)—N(2)—N(3)—C(8) | −177.4(2) |
| C(8)—C(9)—C(14)—C(13) | 179.4(2) | C(5)—N(2)—C(4)—N(1) | 177.2(2) |
| C(11)—C(12)—C(13)—C(14) | 1.7(4) | C(5)—N(2)—C(4)—C(3) | −2.2(4) |
| C(4)—N(1)—C(8)—N(3) | 0.1(3) | C(17)—C(16)—C(18)—F(1) | −3.6(4) |
| C(4)—N(1)—C(8)—C(9) | 179.8(2) | C(17)—C(16)—C(15)—O(1) | −48.5(3) |
| C(4)—N(2)—N(3)—C(8) | 0.2(3) | | |

Example 3: Preparation of Crystal Form a of Compound of Formula (IV)

The compound of formula (IV) (50 mg) was added to ethyl acetate (1 mL) and slurried at 40° C. for 48 hours. The mixture was cooled to 20-25° C. and filtered, and the solid was collected. The solid was dried in vacuum at 40° C. for 48 hours to obtain the crystal form A of the compound of formula (IV).

Example 4: Preparation of Crystal Form B of Compound of Formula (IV)

The compound of formula (IV) (50 mg) was added to methyl tert-butyl ether (1 mL) and slurried at 50° C. for 48 hours. The mixture was cooled to 20-25° C. and filtered, and the solid was collected. The solid was dried in vacuum at 40° C. for 48 hours to obtain the crystal form B of the compound of formula (IV).

Example 5: Study of the Stability of Crystal Form B of the Compound of Formula (IV)

An electronic balance was used to accurately weigh 60 mg sample of crystal form B of compound (IV) (3 samples in parallel for each stability test condition). The samples were placed in a dry and clean 5 mL beaker and spread into a thin layer. The aluminum foil was pierced with holes and placed on the beaker, fixed with rubber bands. The beaker was placed in tbc environment of various stability test conditions and remained for sampling at investigation time. The samples were investigated at 60° C. (5 days, 10 days), 25° C./92.5% RH (5 days, 10 days), 40° C./75% RH (one month, two months, three months), 60° C./75% RH (one month, two months) and light (10 days) conditions. X-ray powder diffraction (XRPD) was used to characterize the solid under various conditions.

TABLE 8

The solid stability test results of the crystal form B of the compound of formula (IV)

| Test condition | Time point | Crystal form |
| --- | --- | --- |
| | 0 days | B |
| High temperature (60° C., open) | 5 days | B |
| | 10 days | B |
| High humidity (room temperature/reiative humidity 92.5%, open) | 5 days | B |
| | 10 days | B |
| High temperature and high humidity (40° C./relative humidity 75%, open) | one mont | B |
| | two months | B |
| | three moths | B |
| High temperature and high humidity (60° C./relative humidity 75%, open) | one month | B |
| | two months | B |
| Light (total illuminance = 1.2 × 10⁶ Lux, near ultraviolet = 200 watts · hour/square meter, sealed) | 10 days | B |

Conclusion: crytal form B of the compound of formula (IV) has good stability under high temperature, high humidity and strong light conditions.

Experimental Example 1: In Vitro Assay

Human VAP-1 Enzyme Activity Assay:
Amplex® Red Monoamine Oxidase Kit (Invitrogen #A12214) was used to determine the inhibitory effects of the sample on VAP-1 enzyme activity. 100 nL Test compound (the solvent was DMSO) that had been gradiently diluted was added to a 384-well plate. 25 μL 10 nM VAP-1 enzyme solution was added, and the solution was incubated at room temperature for 30 minutes. The substrate mixture which had been added with VAP-1 enzyme (200 μM Amplex Red, 1 U/mL HRP, 1 mM Benzylamine) was incubated at room temperature for 60 minutes. After the incubation, the fluorescence signal was read with a microplate reader Envision (excitation light wavelength 530-560 nm, emission light wavelength 590 nm). The fluorescence signal value after removing the background signal was analyzed with Prism software. The $IC_{50}$ of the sample to the VAP-1 enzyme was calculated.

TABLE 9

Result of in vitro screening assay for compound of formula (IV)

| Compound | Human recombinant VAP-1/SSAO enzyme inhibitory activity IC50(nM) |
| --- | --- |
| Compound of formula (IV) | 1.2 |
| Crystal form B of the compound of formula (IV) | 0.71 ± 0.21 |

Conclusion: the compound of formula (IV) and its crystal form B showed strong inhibitory activity against human recombinant VAP-1/SSAO enzyme in in vitro assay.

Experimental Example 2: VAP-1 Cell Activity Assay

Amplex® Red Monoamine Oxidase Kit (Invitrogen #A12214) was used to determine the inhibitory effect of the sample on VAP-1 enzyme activity.
Cell Preparation
The HUVEC or CHO cells were plated onto a 6-well plate at a density of 0.8M/well, placed in a 37° C., 5% $CO_2$ incubator for 24 hours, and then transfected with Lipo2000 reagent and VAP-1/pCDNA (3.1) plasmid. The medium was changed after 5 h (Lipo2000 is toxic to cells). After 24 h, the cells digested and plated into a 384-well plate at a density of 25 μl, 10000 cells/well, 6-7 h, and the cell medium was changed to the medium without FBS and the cell plate was placed in a 37° C. 5% $CO_2$ incubator overnight.
Compound Half Inhibitory Concentration Determination
1) Compound dilution: 4-fold serial dilution with 100% DMSO and diluted at 10 points. The initial concentration of the test compound was 0.5 mM (final concentration was 1 μM); ECHO was used to transfer 100 nL of the compound solution to a 384-well cell detection plate. Negative control well: 100 nL DMSO; background control well: 100 nL DMSO+25 μL medium.
2) Reaction was kept for 30 minutes at room temperature and protected from light.
3) Amplex Red reagent+HRP+benzylamine substrate working solution preparation:
Amplex Red reagent+HRP+benzylamine substrate working solution (200 μM Amplex Red reagent+1 U/mL HRP+1 mM benzylamine): 45 μL of 20 mM Amplex Red reagent mother liquor, 22.5 μL of 200 U/mL horseradish peroxidase (HRP) mother liquor and 45 μL of 100 mM benzylamine were added to 4.3875 mL of 1× reaction buffer.
4) After 30 minutes, 25 μL of the substrate working solution was added to a 384-well plate. The final concentration was 100 μM Amplex Red reagent+0.5 U/mL HRP+0.5 mM benzylamine.

5) The reaction was kept at room temperature and protected from light for 60 minutes, and the fluorescence value was measured with Envision: the excitation wave was 535 nm, and the emission wave was 590 nm.
6) Inhibition rate calculation formula: % inhibition rate= (1−(experimental hole with background deduction-positive control hole with background deduction)/ (negative control hole with background deduction-positive control hole with background deduction))*100
7) Prism was used to analyze the data, and the $IC_{50}$ of the sample against VAP-1 cells was calculated.

TABLE 10

| In vitro screening assay result of the compounds of the present invention | |
|---|---|
| Compound | VAP-1/SSAO cell activity assay test $IC_{50}$(nM) |
| Compound of formula (IV) | 1.3 |
| Crystal form B of the compound of formula (IV) | 2.2 ± 1.49 |

Conclusion: the compound of formula (IV) and its crystal form B showed strong inhibitory activity against VAP-1/SSAO cells in in vitro assays.

What is claimed is:

1. A crystal form A of a compound of formula (IV), wherein the X-ray powder diffraction (XRPD) pattern thereof has characteristic diffraction peaks at the following 2θ angles: 9.05±0.2°, 12.34±0.2°, and 22.52±0.2°,

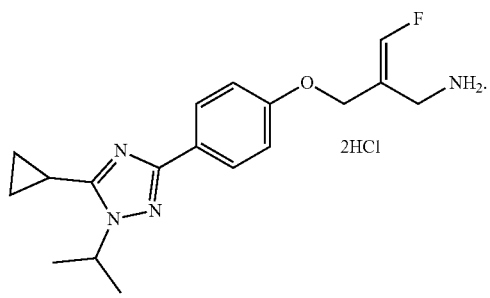

(IV)
2HCl

2. The crystal form A of the compound of formula (IV) as defined in claim 1, wherein the XRPD pattern thereof has characteristic diffraction peaks at the following 2θ angles: 9.05±0.2°, 12.34±0.2°, 16.60±0.2°, 17.17±0.2°, 17.83±0.2°, 20.82±0.2°, 22.52±0.2°, 26.03±0.2°, and/or
   wherein the differential scanning calorimeter (DSC) curve thereof has an endothermic peak at 223.0° C.±3.0° C., and/or
   wherein the thermogravimetric analysis curve (TGA) thereof shows a weight loss of 3.78% at 150.0° C.±3° C.

Figure 2:
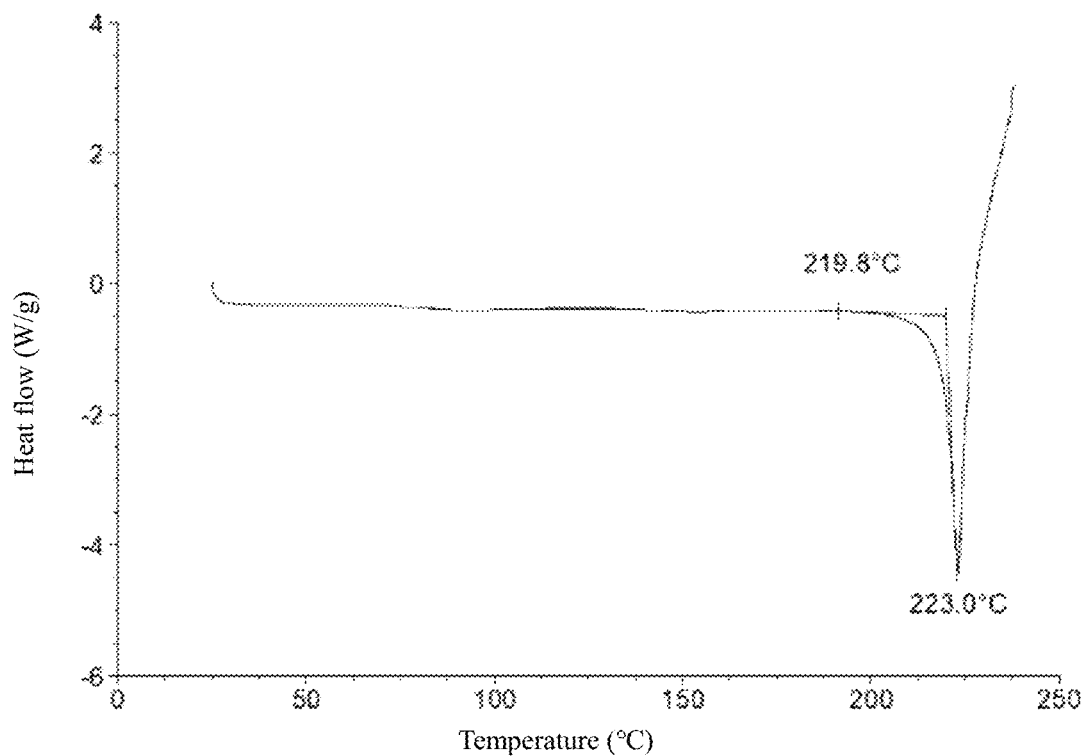
FIG. 2 is a DSC pattern of crystal form A of the compound of formula (IV).
Figure 3:
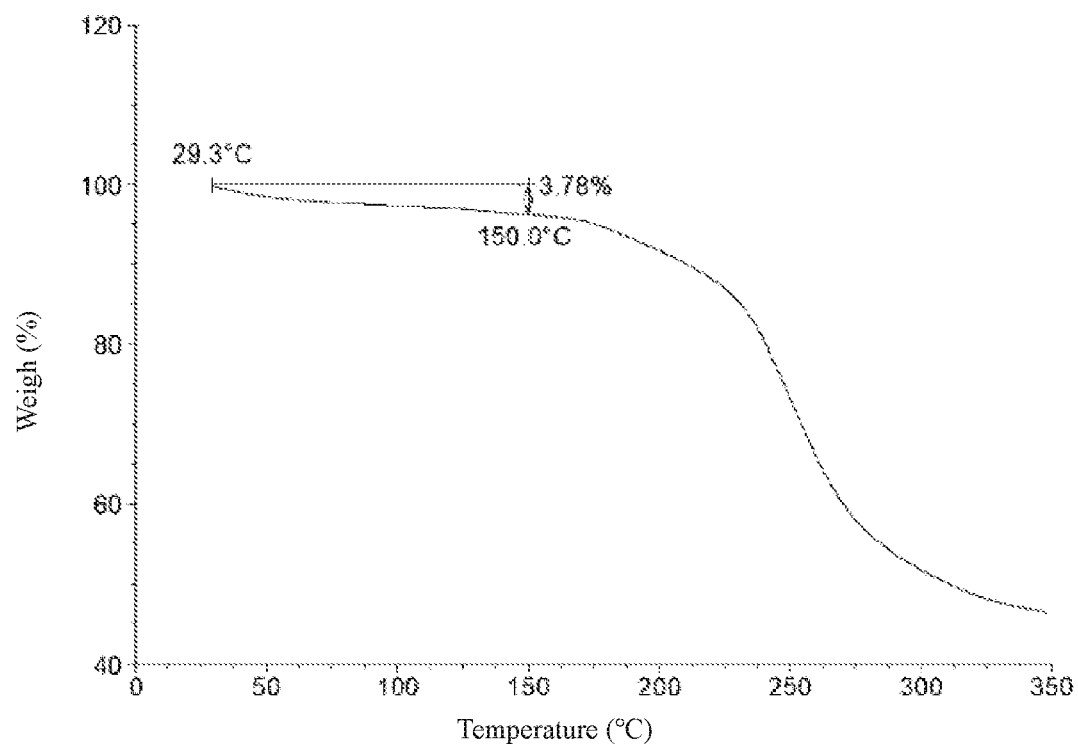
FIG. 3 is a TGA diagram of crystal form A of the compound of formula (IV).

3. The crystal form A of the compound of formula (IV) as defined in claim 2, wherein the XRPD pattern thereof is as shown in FIG. 1, and/or
   wherein the DSC pattern thereof is as shown in FIG. 2, and/or
   wherein the TGA pattern thereof is as shown in FIG. 3.

4. A preparation method of the crystal form A of the compound of formula (IV) as defined in claim 1, comprising adding any one of the forms of the compound of formula (IV) to an organic solvent containing an ester or ether to prepare a slurry, wherein the temperature for preparing the slurry ranges from 20° C. to 40° C.

5. The preparation method as defined in claim 4, wherein the ester is ethyl acetate, and the ether is methyl tert-butyl ether, and/or
   wherein a time used for preparing the slurry ranges from 30 hours to 60 hours; and/or
   wherein a weight ratio of the compound of formula (IV) to the organic solvent ranges from 1:5-40.

6. A crystal form B of a compound of formula (IV), wherein the X-ray powder diffraction (XRPD) pattern thereof has characteristic diffraction peaks at the following 2θ angles: 11.27±0.2°, 21.44±0.2°, 22.32±0.2°,

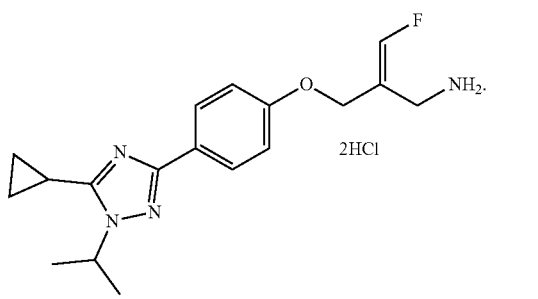

(IV)
2HCl

7. The crystal form B of the compound of formula (IV) as defined in claim 6, wherein the XRPD pattern thereof has characteristic diffraction peaks at the following 2θ angles: 11.27±0.2°, 12.46±0.2°, 18.44±0.2°, 21.44±0.2°, 22.32±0.2°, 25.51±0.2°, 25.94±0.2°, 26.49±0.2°.

8. The crystal form B of the compound of formula (IV) as defined in claim 7, wherein the XRPD pattern thereof has characteristic diffraction peaks at the following 2θ angles: 11.27±0.2°, 12.46±0.2°, 18.44±0.2°, 20.03±0.2°, 21.44±0.2°, 22.32±0.2°, 23.37±0.2°, 24.19±0.2°, 25.51±0.2°, 25.94±0.2°, 26.49±0.2°, 28.12±0.2°, and/or
   wherein the differential scanning calorimeter (DSC) curve thereof has an endothermic peak at 221.9° C.±3.0° C., and/or
   wherein the thermogravimetric analysis curve (TGA) thereof shows a weight loss of 1.05% at 150.0° C.±3° C.

Figure 4:
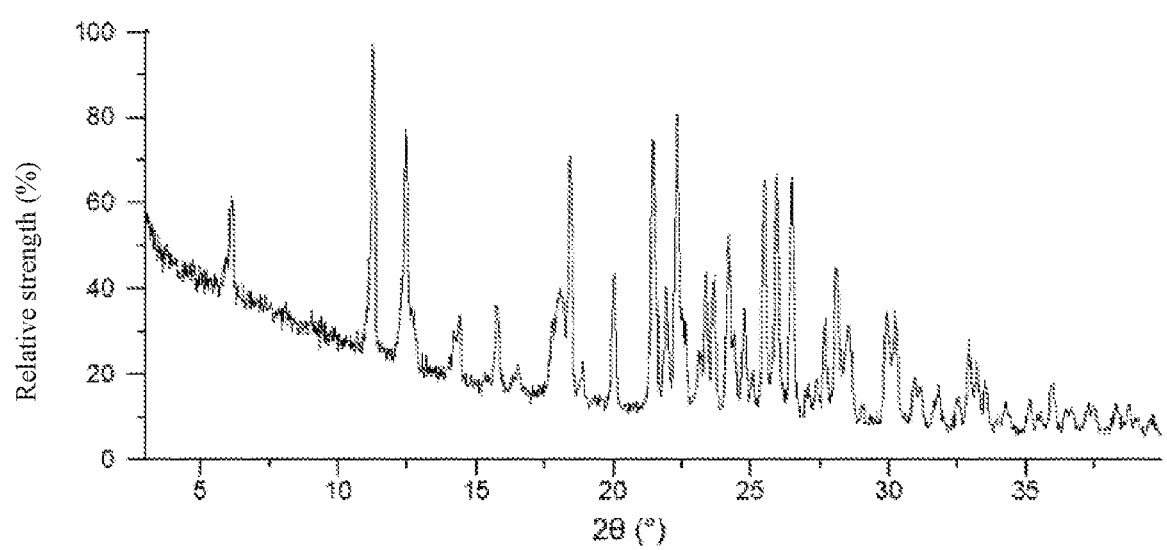
FIG. 4 is an XRPD spectrum of Cu-Kα radiation of crystal form B of the compound of formula (IV).
Figure 5:
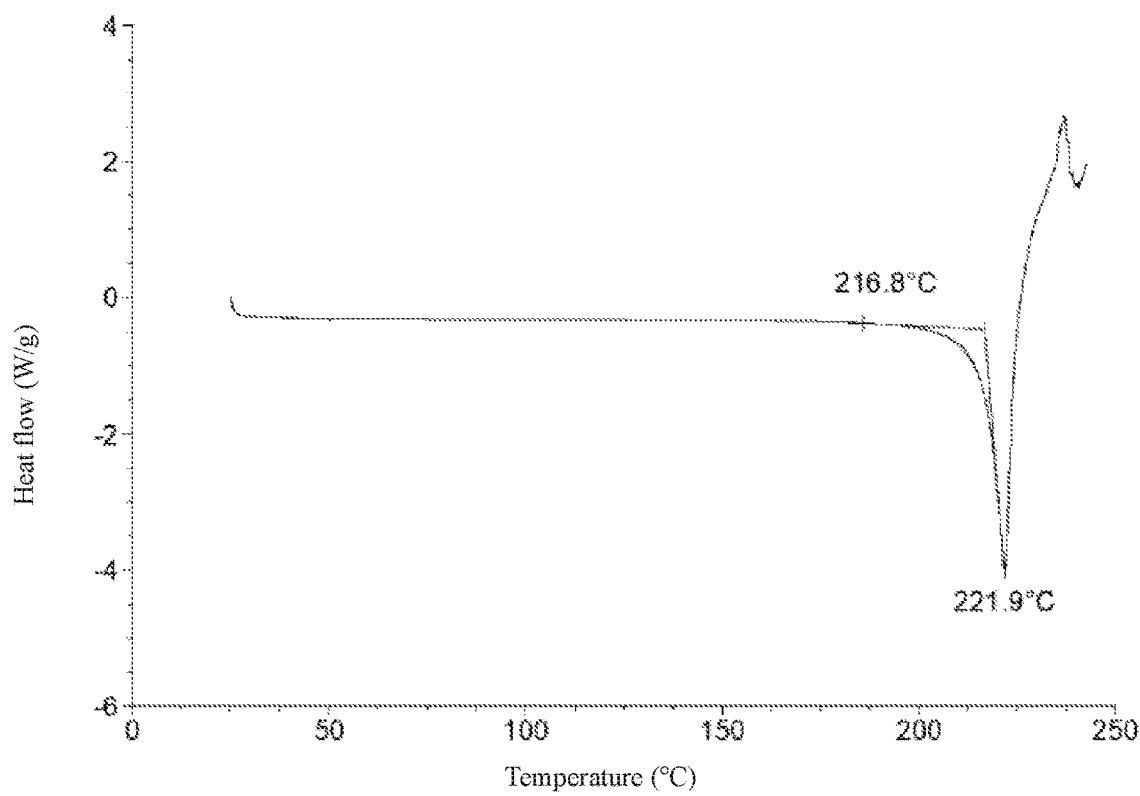
FIG. 5 is a DSC pattern of crystal form B of the compound of formula (IV).
Figure 6:
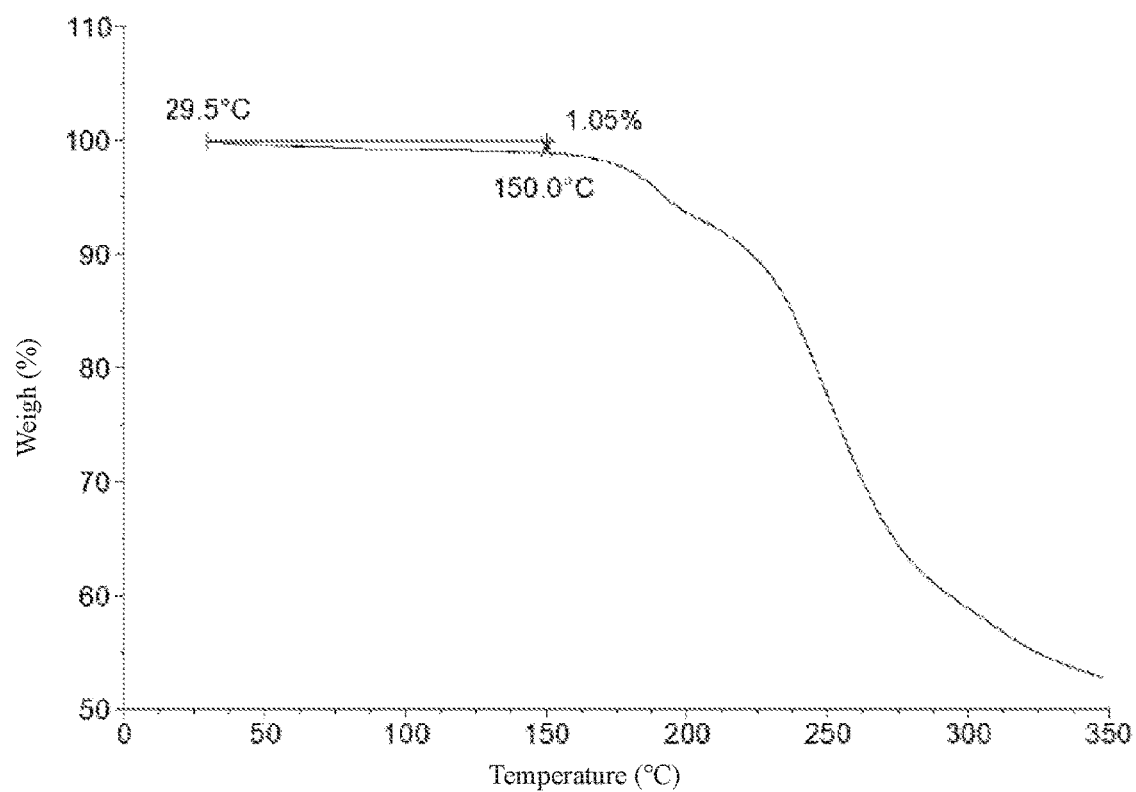
FIG. 6 is a TGA diagram of crystal form B of the compound of formula (IV).

9. The crystal form B of the compound of formula (IV) as defined in claim 8, wherein the XRPD pattern thereof is as shown in FIG. 4, and/or
   wherein the DSC pattern thereof is as shown in FIG. 5, and/or
   wherein the TGA pattern thereof is as shown in FIG. 6.

10. A preparation method of the crystal form B of the compound of formula (IV) as defined in claim 6, comprising adding any one of the forms of the compound of formula (IV) to an ester, ether, alcohol, acetone, acetonitrile, n-heptane, water, mixed organic solvent, or a mixture of water and organic solvent to prepare a slurry, wherein the temperature for preparing the slurry ranges from 40° C. to 60° C.

11. The preparation method of the crystal form B of the compound of formula (IV) as defined in claim 10, wherein the ester is ethyl acetate, the ether is selected from the group consisting of tetrahydrofuran and methyl tert-butyl ether, the alcohol is ethanol, the mixed organic solvent is selected from the group consisting of a mixture of methyl tert-butyl ether and methanol with a volume ratio of 95:5 and a mixture of methyl tert-butyl ether and ethanol with a volume ratio of 95:5, the mixture of water and organic solvent is selected from the group consisting of a mixture of water and acetone with a volume ratio of 5:95, a mixture of water and acetonitrile with a volume ratio of 5:95, and a mixture of water and tetrahydrofuran with a volume ratio of 5:95, and/or wherein a time used for preparing the slurry ranges from 30 hours to 60 hours; and/or wherein a weight ratio of the compound of formula (IV) to the mixed organic solvent ranges from 1:5-40.

12. A method for treating a semicarbazide-sensitive amine oxidase-associated (SSAO-associated) disease in a subject in need thereof, comprising administering an effective amount of the crystal form A as defined in claim 1 to the subject, wherein, the SSAO-associated disease is non-alcoholic steatohepatitis.

13. A preparation method of a compound of formula (IV),

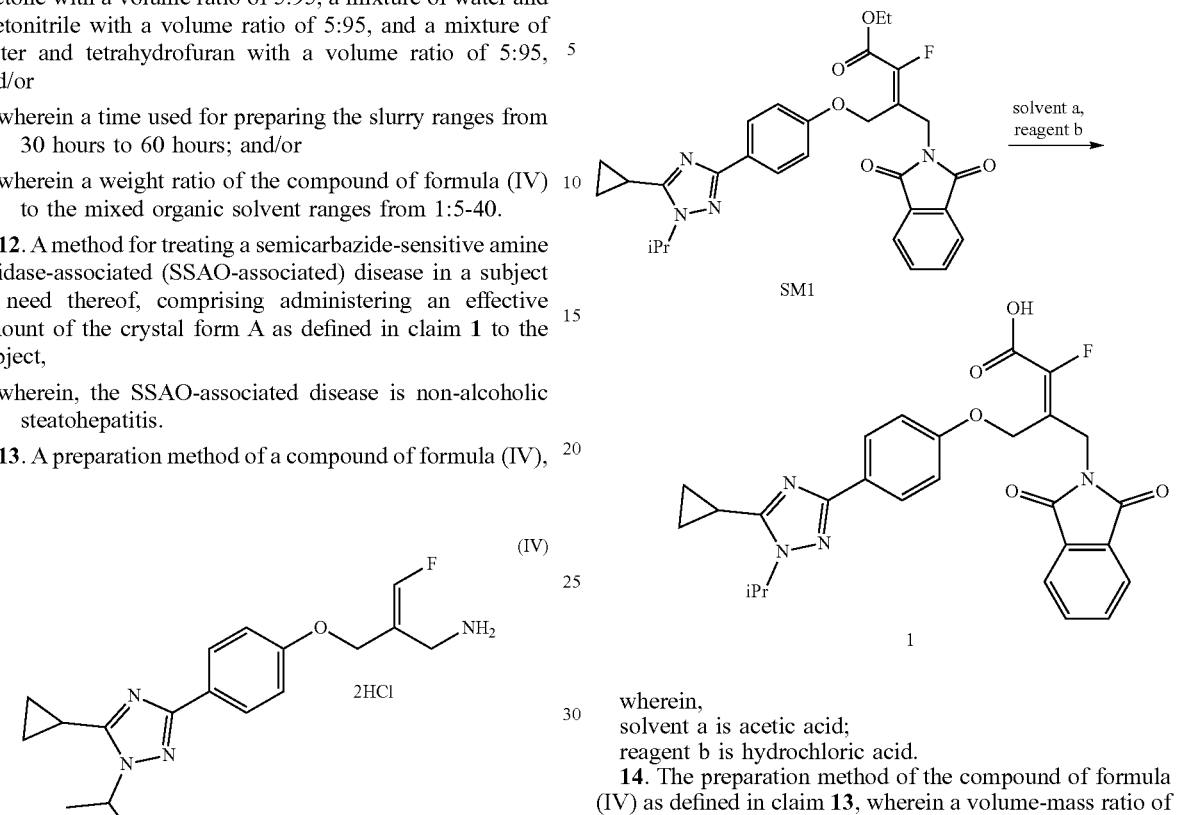

which comprises:

wherein,
solvent a is acetic acid;
reagent b is hydrochloric acid.

14. The preparation method of the compound of formula (IV) as defined in claim 13, wherein a volume-mass ratio of solvent a to SM1 is 3.0 to 3.5:1, and a volume-mass ratio of solvent b to SM1 is 3.0 to 10:1, and/or wherein an internal temperature of the reaction is controlled at 75-80° C.; and/or wherein the method further comprises the following steps:

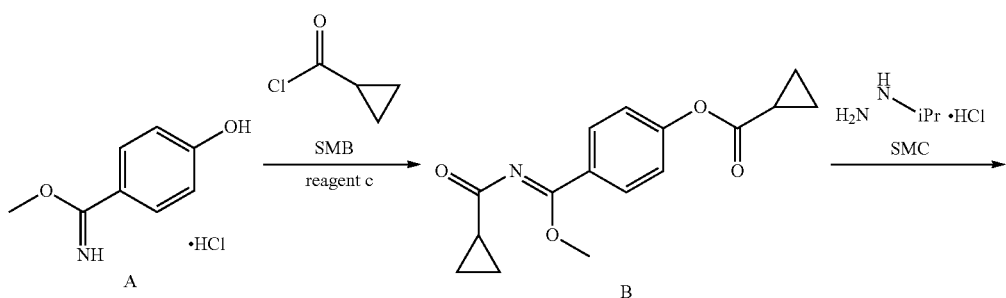

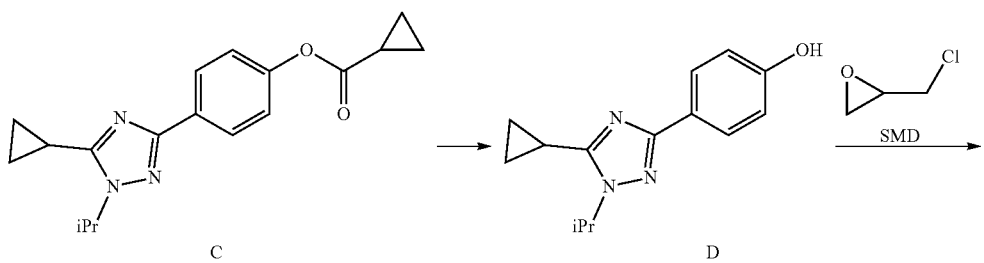

-continued
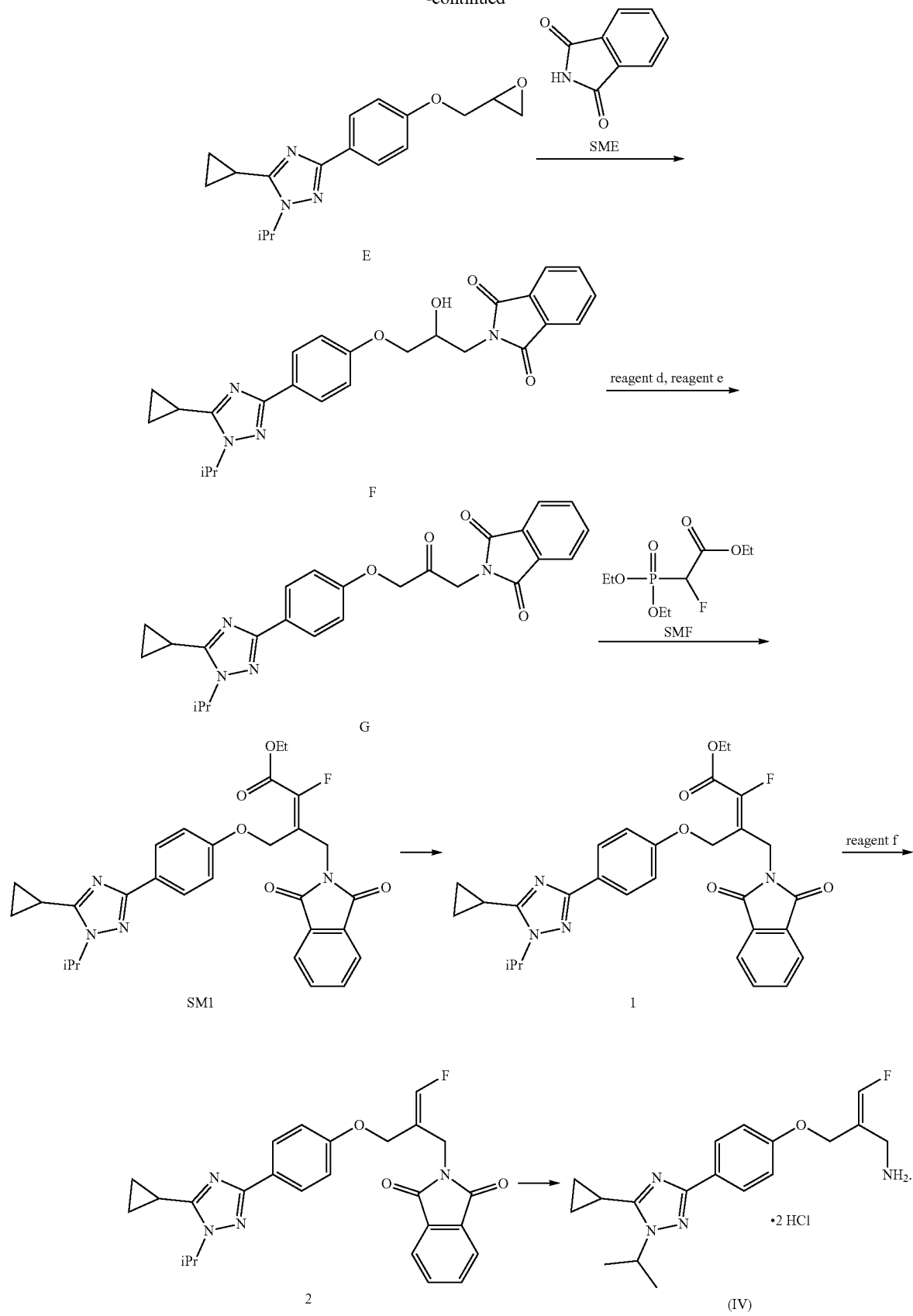

15. The preparation method of the compound of formula (IV) as defined in claim 14, wherein reagent c is pyridine; compound D is prepared through hydrolysis reaction under alkaline conditions; reagent d is potassium bromide, reagent e is sodium hypochlorite; and reagent f is silver acetate.

16. A method for treating a semicarbazide-sensitive amine oxidase-associated (SSAO-associated) disease in a subject in need thereof, comprising administering an effective amount of the crystal form B as defined in claim 6 to the subject;

wherein, the SSAO-associated disease is non-alcoholic steatohepatitis.

* * * * *

UNITED STATES PATENT AND TRADEMARK OFFICE
CERTIFICATE OF CORRECTION

| | |
|---|---|
| PATENT NO. | : 12,077,513 B2 |
| APPLICATION NO. | : 17/311431 |
| DATED | : September 3, 2024 |
| INVENTOR(S) | : Zhi Luo et al. |

It is certified that error appears in the above-identified patent and that said Letters Patent is hereby corrected as shown below:

In the Specification

At Column 30, 4th formula, "OEt" should be --OH--.

Signed and Sealed this
Twenty-ninth Day of October, 2024

*Katherine Kelly Vidal*

Katherine Kelly Vidal
*Director of the United States Patent and Trademark Office*